US 8,073,212 B2

United States Patent
Gerlach et al.

(10) Patent No.: US 8,073,212 B2
(45) Date of Patent: Dec. 6, 2011

(54) METHODS AND PRODUCTS FOR ANALYZING GINGIVAL TISSUES

(75) Inventors: Robert Woodrow Gerlach, Cincinnati, OH (US); Roger David Gibb, Mason, OH (US); Michael Eugene Rubush, West Chester, OH (US); John Michael Dunavent, Loveland, OH (US); Stephen Francis McClanahan, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1014 days.

(21) Appl. No.: 11/880,908

(22) Filed: Jul. 25, 2007

(65) Prior Publication Data

US 2008/0026340 A1    Jan. 31, 2008

Related U.S. Application Data

(60) Provisional application No. 60/833,281, filed on Jul. 25, 2006.

(51) Int. Cl.
*G06K 9/00* (2006.01)
*G06K 9/34* (2006.01)
*G06K 9/46* (2006.01)
*G06K 9/66* (2006.01)

(52) U.S. Cl. ......... 382/128; 382/164; 382/165; 382/195

(58) Field of Classification Search ................. None
See application file for complete search history.

(56) References Cited

U.S. PATENT DOCUMENTS

| | | | |
|---|---|---|---|
| 6,190,170 B1 | 2/2001 | Morris et al. | |
| 6,571,003 B1 * | 5/2003 | Hillebrand et al. | 382/118 |
| 6,793,489 B2 | 9/2004 | Morris et al. | |
| 7,168,954 B2 * | 1/2007 | Charles et al. | 434/263 |
| 7,324,661 B2 * | 1/2008 | Kemp et al. | 382/100 |
| 2003/0156788 A1 | 8/2003 | Henning | |
| 2004/0236232 A1 | 11/2004 | Jonusauskas et al. | |

FOREIGN PATENT DOCUMENTS

WO   WO 2004/093673 A1   11/2004

OTHER PUBLICATIONS

Miller, et al., "A Digital Image Analysis Technique for Assessing Gingivitis" (DIAG), Research presented at the 76th General Session of the IADR; Nice, France Jun. 24-27, 1998.*

(Continued)

*Primary Examiner* — Tom Y Lu
*Assistant Examiner* — Thomas Conway
(74) *Attorney, Agent, or Firm* — Julia A. Glazer; James C. Vago; David M. Weirich

(57) ABSTRACT

A system and method employing image analysis may provide an objective measure of the state of gingival tissue health. A region of analysis on an image of gingival tissue may be divided into pixels. Each pixel may have an associated color made up of component R, G and B values. A user may obtain an objective measurement of oral cavity soft tissue health by determining an objective measurement of the component color values of a gingival tissue image region and performing statistical analysis on the color values.

34 Claims, 16 Drawing Sheets
(16 of 16 Drawing Sheet(s) Filed in Color)

OTHER PUBLICATIONS

Barker, M.L., et al., "Subject-Level Meta-Analysis of Clinical Effectiveness for Direct-to Consumer Vital Bleaching Products," Presented at the 82nd General Session of the IADR, Mar. 2004.*

Bellamy, P., et al., "Clinical Tooth Whiting Measured by Digital Imaging and Commercial Spectrophotometers," Presented at the 84th General Session of the AADR, Mar. 2006, p. 1.*

Barker, M.L., et al., "Tooth Color Measurement Reproducibility and Examiner Reliability Using Digital Imaging," Presented at the 83rd General Session of the IADR, Mar. 2005, p. 1.*

Iiyama, M., et al., "Applicability of a Computer-Assisted Image Analysis System for the Evaluation of Gingival Status in Subjects from Asian and Caucasian Backgrounds," Journal Int Acad Periodontal, 2002, vol. 4, Issue 1, pp. 26-32.*

American Dental Association, "Guide to Digital Dental Photography and Imaging," 2003, pp. 1-53.

Archila, L., et al., "Association Between Clinical and Photoimagin Scores for Gingivitis," Abstract 1068, IADR/AADR/CADR 83$^{rd}$ General Session, 2005, p. 1.

Barker, M.L., et al., "Alternative Statistical Method for Comparing Overall Color Change," Presented at the 80$^{th}$ General Session of the IADR, Mar. 2002, pp. 1-2.

Barker, M.L., et al., "Prediction of Subjective Response from Objective Color Change in a Bleaching Clinical Trial," Presented at the 32$^{nd}$ Annual Meeting of the AADR, Mar. 2003, p. 1.

Barker, M.L., et al., "Subject-Level Meta-Analysis of Clinical Effectiveness for Direct-to Consumer Vital Bleaching Products," Presented at the 82$^{nd}$ General Session of the IADR, Mar. 2004.

Barker, M.L., et al., "Tooth Color Measurement Reproducibility and Examiner Reliability Using Digital Imaging," Presented at the 83$^{rd}$ General Session of the IADR, Mar. 2005, p. 1.

Barker, M.L., et al., "Clinical Trial Comparing Initial and Sustained Tooth Color Using Strips," Presented at the 84$^{th}$ General Session of the AADR, Mar. 2006, p. 1.

Baumgartner, W., et al., "The Diagnostic Value of Redness in Gingivitis," p. 32-35.

Bellamy, P., et al., "Clinical Tooth Whiting Measured by Digital Imaging and Commercial Spectrophotometers," Presented at the 84$^{th}$ General Session of the AADR, Mar. 2006, p. 1.

Bergström, J., "Vascular Reaction in Plaque-Induced Gingivitis: A Quantitative Approach," Journal of Periodontal Research, 1992, vol. 27, pp. 604-608.

Ferrari, M., et al., "Daytime use of a Custom Bleaching Tray or Whiting Strips: Initial and Sustained Color Improvement," American Journal of Dentistry, 2007, vol. 20, pp. 19A-22A.

Gerlach, R.W., et al., "Clinical Response of Maxillary and Mandibular Teeth Following Use of 6.5% Hydrogen Peroxide Whitening Strips," Presented at the 80$^{th}$ General Association of the IADR, Mar. 2002, p. 1.

Gerlach, R.W., et al., "Clinical Study of Barrier Usage in Peroxide-Based Tooth Whitening," Presented at the 83$^{rd}$ General Session of the IADR, Mar. 2005, p. 1.

Gerlach, R.W., et al., "Clinical Whitening of Dentifrice and Paint-One Gel Versus Tray Control," Presented at the 83$^{rd}$ General Session of the IADR, Mar. 2005, p. 1.

Gerlach, R.W., et al., "Clinical Trail of Direct-to-Consumer and Professional Whitening Strips," Presented at the 84$^{th}$ General Session of the AADR, Mar. 2006, p. 1.

Gerlach, R.W.; "Tooth Whitening Clinical Trials: A Global Perspective," American Journal of Dentistry, 2007, vol. 20, Special Issue A, pp. 3A-6A.

Gibb, R.D., et al., "Spatial Whitening Response with 6.5% Hydrogen Peroxide Whitening Strips," Presented at the 32$^{nd}$ Annual Meeting of the AADR, Mar. 2003, p. 1.

Haerian, H.A., et al., "Measuring the True Color of Human Gingiva; A Spectrophotometric Assessment of Gingival Color and Clinical Gingivitis," Journal of Dental Research, 2002, vol. 81, Special Issue A, Article 0979.

Hanioka, T., et al., "Haemoglobin Concentration and Oxygen Saturation in Dog Gingiva with Experimentally Induced Periodontitis," Archs Oral Bio., 1989, vol. 34, No. 8, pp. 657-663.

Hanioka, T., et al., "Changes in Hemoglobin Concentration and Oxygen Saturation in Human Gingiva with Decreasing Inflammation," Journal of Periodontol, 1991, vol. 62, No. 6, pp. 366-369.

Hanioka, T., et al., "Changes in Oxygen Consumption in Dog Gingiva During Induction of Experimental Periodontitis," Journal of Dental Research, 1992, vol. 71, No. 3, pp. 466-469.

Hanioka, T., et al., "Oxygen Sufficiency in the Gingiva of Smokers and Non-Smokers with Periodontal Disease," Journal of Periodontol, 2000, vol. 71, No. 12, pp. 1846-1851.

Hernández, J.C., et al., "Professional Whitening Strips in a University Population," American Journal of Dentistry, 2007, vol. 20, Special Issue, 15A-18A.

Hock, J., et al., "A Vital Microscopy Study of the Morphology of Normal and Inflamed Gingiva," Journal of Periodontal Research, 1971, vol. 6, pp. 81-88.

Jones, J., et al., "A Photometric Study of color of Healthy Gingiva," Journal of Periodontal, 1977, pp. 21-26.

Loe, H., et al., "Periodontal Disease in Pregnancy I. Prevalence and Severity," ATA Odont Scand, 1963, vol. 21, pp. 533-551.

Nuki, K., et al., "The Organisation of the Gingival Vasculature," Journal of Periodontal Research, 1974, vol. 9, pp. 305-313.

Sagal, P., et al., "Application of Digital Imaging in Tooth Whitening Radomized Controlled Trials," American Journal of Dentistry, 2007, vol. 20, pp. 7A-14A.

Shizukuishi, S., et al., "Clinical Application of Tissue Reflectance Spectrophotometry to Periodontal Disease," Adv. Dent. Research, 1988, vol. 2, Issue 2, pp. 389-394.

Shizukuishi, H.T., et al., "Hemoglobin Concentration and Oxygen Saturation of clinically Healthy and Inflamed Gingiva in Human Subjects," Journal of Periodontal Research, 1990, vol. 25, pp. 93-98.

Söderhold, G., et al., "Morphological Changes in Gingival Blood Vessels During Developing Gingivitis in Dogs," Journal of Periodontal Research, 1973, vol. 8, pp. 16-20.

Tanaka, M., et al., "Association of Oxygen Tension in Human Periodontal Pockets with Gingival Inflammation," Journal of Periodontal, 1998, vol. 69, No. 10, pp. 1128-1130.

Tanaka, M., et al., "Effect of Mechanical Toothbrush Stimulation on Gingival Microcirculatory Functions in Inflames Gingiva of Dogs," Journal of Periodontology, 1998, vol. 25, pp. 561-565.

White, D.J., et al., "Antiplaque Efficacy of Combined Chemotherapeutics," Presented at the 85$^{th}$ General Session of the IADR, 2007, p. 1.

International Search Report, Application No. PCT/IB2007/052965, date of mailing Jun. 9, 2008.

International Search Report and Written Opinion, Application No. PCT/IB2007/052965, date of mailing Jul. 31, 2008.

Nasir Mansjur, et al., "New Method Using Image Analysis to Measure Gingival Color," Journal of the Osaka Dental University, vol. 38, No. 1, Apr. 2004, pp. 37-40.

"A Digital Image Analysis Technique for Assessing Gingivitis" (DIAG), Research presented at the 76$^{th}$ General Session of the IADR; Nice, France Jun. 24-27, 1998.

Slides shown during oral presentation entitled, "A Digital Image Analysis Technique for Assessing Gingivitis" (DIAG), Research presented at the 76$^{th}$ General Session of the IADR; Nice, France Jun. 24-27, 1998.

* cited by examiner

1610

| | | | | Change from Baseline[c] | | | |
|---|---|---|---|---|---|---|---|
| Visit | N | Mean (SD) | Correlation with Baseline[a,b] | Mean (SD) | Median | Min..Max. | P-value |
| First Hygiene Phase | | | | | | | |
| Day -14 | 20 | 125.8 (10.60) | | | | | |
| Day -7 | 19 | 133.9 (10.29) | 0.89 (<0.001) | 8.6 (8.12) | 9.1 | -4.9 - 21.4 | <0.001 |
| Day 0 | 20 | 137.4 (10.95) | 0.79 (<0.001) | 11.6 (9.67) | 10.4 | -0.7 - 36.6 | <0.001 |
| Experimental Gingivitis Phase | | | | | | | |
| Day 0 | 20 | 137.4 (10.95) | | | | | |
| Day 7 | 20 | 133.7 (12.79) | 0.88 (<0.001) | -3.7 (6.97) | -2.7 | -17.9 - 6.7 | 0.012 |
| Day 14 | 20 | 133.0 (10.02) | 0.93 (<0.001) | -4.4 (4.06) | -5.2 | -12.2 - 3.2 | <0.001 |
| Day 21 | 20 | 126.7 (10.79) | 0.71 (<0.001) | -10.7 (8.21) | -10.9 | -26.2 - 5.1 | <0.001 |
| Second Hygiene Phase | | | | | | | |
| Day 21 | 20 | 126.7 (10.79) | | | | | |
| Day 28 | 20 | 125.0 (12.08) | 0.89 (<0.001) | -1.7 (5.47) | -2.6 | -9.0 - 11.2 | 0.178 |
| Day 35 | 19 | 134.1 (8.65) | 0.78 (<0.001) | 6.4 (6.52) | 7.6 | -6.9 - 21.8 | <0.001 |
| Day 42 | 19 | 136.7 (10.96) | 0.64 (0.003) | 9.9 (8.88) | 8.1 | -2.3 - 32.5 | <0.001 |

[a] Baseline refers to the first visit in each phase: Day -14 for the first hygiene phase, Day 0 for the experimental gingivitis phase and Day 21 for the second hygiene phase.
[b] Pearson correlation coefficient (p-value).
[c] Two sided p-value from a paired difference t-test.

FIG. 16

METHODS AND PRODUCTS FOR ANALYZING GINGIVAL TISSUES

CROSS REFERENCE TO RELATED APPLICATION

This application claims the benefit of U.S. Provisional Application No. 60/833,281, filed Jul. 25, 2006.

FIELD OF THE INVENTION

This patent relates to methods and products for analyzing soft tissues of an oral cavity.

BACKGROUND OF THE INVENTION

Imaging systems for analyzing hard tissues, such as teeth, are known in the art. An example is described in U.S. Patent Application Serial No. 2003/0059381, "Structures and compositions increasing the stability of peroxide actives" to Goodhart, et al. Some methods for analyzing soft tissues of the oral cavity also exist, such as the Löe and Silness Gingival Index as described in "Periodontal Disease in Pregnancy: Prevalence and Severity", the Modified Gingival Index as described in "A modified gingival index for use in clinical trials" by Lobene, et al., and the Ainamo and Bay Gingival Bleeding Index as described in "Problems and proposals for recording gingivitis and plaque" by Ainamo and Bay. However, there is a continuing desire to provide more objective methods and products for analyzing oral cavity soft tissue condition or health. Further, there is a continuing desire to provide methods and products for semi-automated or automated analysis of soft tissues, wherein the methods and products can be used to compare the soft tissues of one or more subjects or to analyze the effect upon soft tissues of one or more products or regimens.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 16 is a tabular example of a displayed result of gingival analysis.

DETAILED DESCRIPTION OF THE INVENTION

Figure 1:
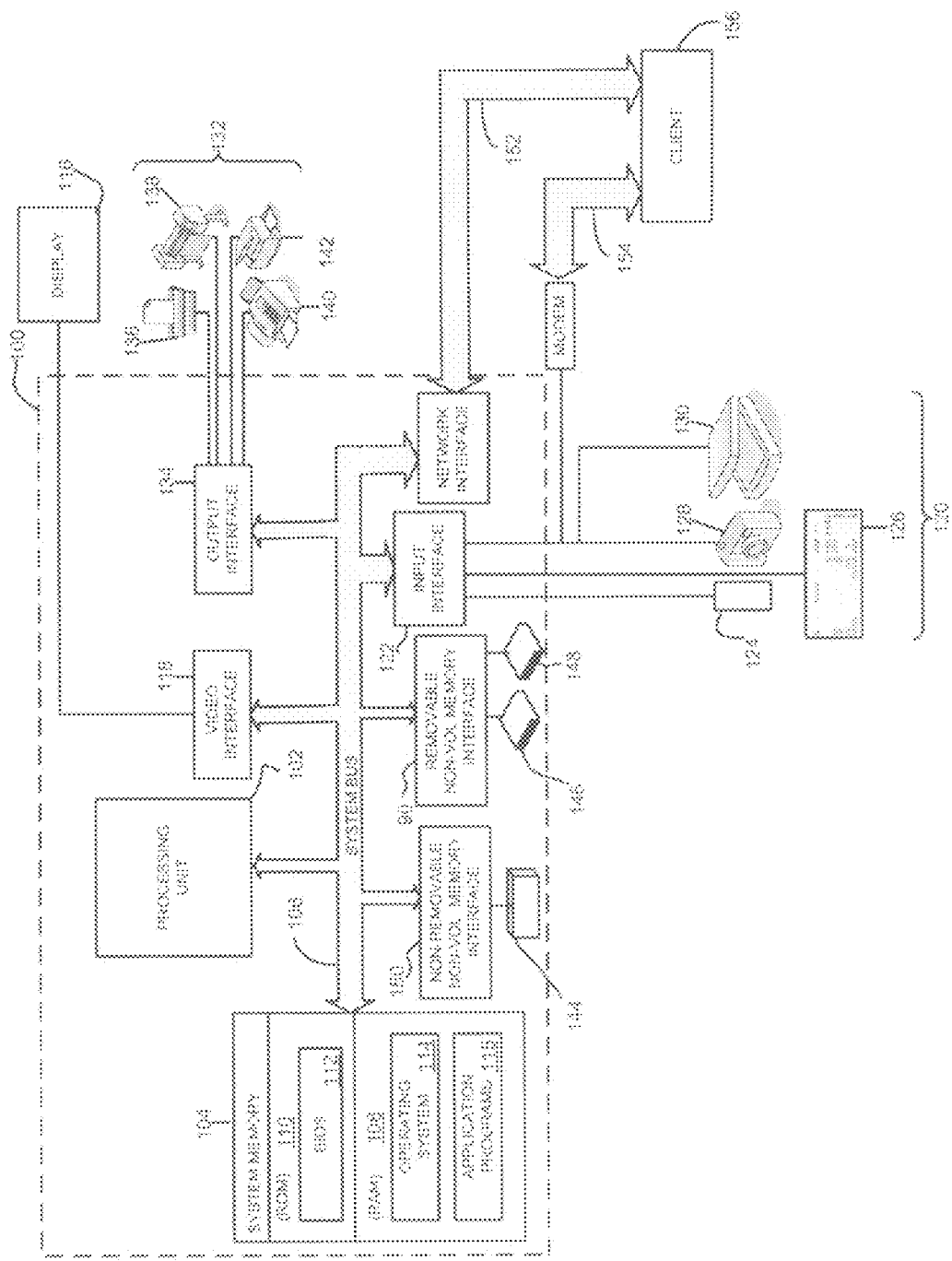
FIG. 1 is an example of a general purpose computer for use with the described method and system.

All documents cited in the Detailed Description are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

There are broadly described herein methods and systems for analyzing soft tissues. A system and method employing image analysis may provide an objective measure of the state or condition of soft tissue. For simplicity of discussion, gingival tissue will be discussed hereafter as an example of soft tissue suitable for use with the present invention. A region of analysis on an image of gingival tissue may be divided into pixels. Each pixel may have an associated color that may be characterized by one or more color values. As used herein, the term "color value" is intended to refer to one or more numeric values that represent a spectral or other color or pixel characteristic. The characteristic associated with the color value is generically referred to as a color characteristic. Examples of color characteristics include components of a color space (e.g., RGB color space, CIELAB color space, and LCH color space), brightness, luminance, hue, saturation, chroma, color temperature, contrast, intensity, lightness, reflectance may have color values. The color value can include, but is not limited to, a single value, a range of values, multiple values, a statistical value, or any value mathematically calculated from several values or from an algorithm. For instance, a gradient or slope derived from several values or a summation of several values can also constitute a color value. For simplicity and ease of discussion, RGB color space component values, referred to herein as R, G, and B, will be discussed most frequently hereafter. In one embodiment, a user may obtain an objective measurement of oral cavity soft tissue health or disease (and other conditions) by determining an objective measurement of one or more component color values of a gingival tissue image region and performing statistical analysis on the color values. Other uses for the present invention may include, but are not limited to, determining the relative safety of a product, drug, or regimen by analyzing the soft tissue for changes in redness which might indicate irritation or other adverse reaction to a product or regimen. For example, the fit, integration, or retention of implants and prosthetics can be evaluated based upon changes in redness of soft tissue, which can be an indication of irritation. In another embodiment, specific regions of the soft tissue may be analyzed. For instance, interproximal gingival tissues may be a region of interest, particularly where changes in redness (or other calorimetric tissue changes) may be useful for determining the effectiveness of particular products or regimens with respect to the interproximal tissues. In yet another use, the safety and/or tolerability of products, such as a denture adhesive, can be evaluated based upon changes in redness.

In one embodiment, the computer-implemented system and methods automatically analyze gingival tissues. In another embodiment, a computer system semi-automatically analyzes gingival tissues and a human user provides some of the analysis and/or inputs to the computer system. While the invention will be described hereafter with respect to automatic and semi-automatic systems and methods, it is contemplated that the invention encompasses systems and methods for manually analyzing gingival tissues, wherein a human user conducts the analysis.

Referring to FIG. 1, a computer system 100 may include a processing unit (CPU) 102, for example, an Intel Pentium™ class microprocessor. One or more memory devices 104 may be connected to a bus 106, including random access memory (RAM) 108 and read only memory (ROM) 110. A basic input/output system (BIOS) 112, containing the routines that may transfer information between elements within the computer 100, is typically stored in ROM 110. RAM 108 typically contains immediately accessible program modules such as the operating system 114 or application programs 115 currently used by the CPU 102. A display 116 may be connected to the system bus 106 though a video interface 118. Input 120 devices may be connected to the system bus 106 though an input interface 122. Input devices may include a mouse 124, a keyboard 126, a camera 128, a scanner 130 or other image capture device. Output 132 devices may be connected to the system bus 106 through an output interface 134 and may include a printer 136, a plotter 138, a facsimile device 140, a photocopier 142, and the like.

The computer system 100 may include a computer-readable medium having a computer program or computer system 100 software accessible therefrom. The computer program may include instructions for performing methods. The computer-readable medium may be stored on a non-removable, non-volatile memory device 144 such as a hard disk, or a removable, non-volatile memory device such as a floppy disk drive 146 or an optical disk drive 148. The non-removable, non-volatile memory device 144 may communicate with the computer 100 system bus 106 through a non-removable, non-volatile memory interface 150. The computer-readable medium may include a magnetic storage medium (disk medium, tape storage medium, microdrives, compact flash cards), an optical storage medium (compact disks such as CD-ROM, CD-RW, and DVD), a non-volatile memory storage medium, a volatile memory storage medium, and data transmission or communications medium including packets of electronic data, and electromagnetic or fiber optic waves modulated in accordance with instructions. Thus, the computer readable medium tangibly embodies a program, functions, and/or instructions that are executable by the computer system 100 to perform methods as described herein.

The computer system 100 may be connected to a network, including local area networks (LANs) 152, wide area networks (WANs) 154, portions of the Internet such as a private Internet, a secure Internet, a value-added network, or a virtual private network. Suitable network clients 156 may include personal computers, laptops, workstations, disconnectable mobile computers, mainframes, information appliances, personal digital assistants, and other handheld and/or embedded processing systems. The signal lines that support communications links to clients 156 may include twisted pair, coaxial, or optical fiber cables, telephone lines, satellites, microwave relays, modulated AC power lines, and other data transmission "wires" known to those of skill in the art. Further, signals may be transferred wirelessly through a wireless network or wireless LAN (WLAN) using any suitable wireless transmission protocol, such as the IEEE series of 802.11 standards. Although particular individual and network computer systems and components are shown, those of skill in the art will appreciate that the present invention also works with a variety of other networks and computers.

Figure 2B:
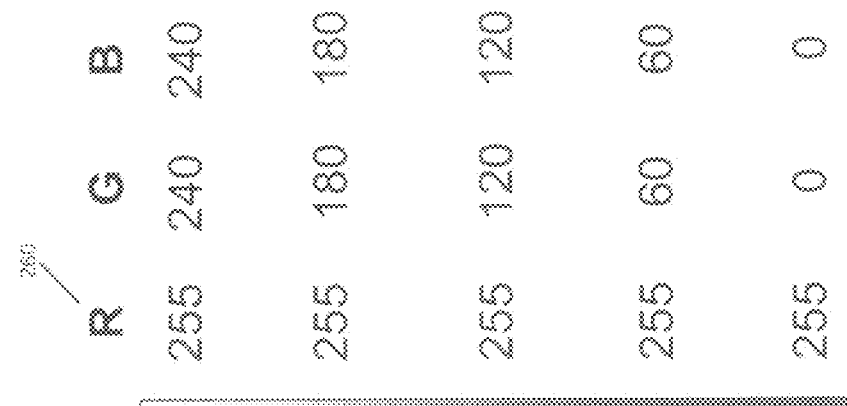
FIG. 2b is an example of a color scale wherein the R value is displayed against varying values of both G and B.
Figure 2A:
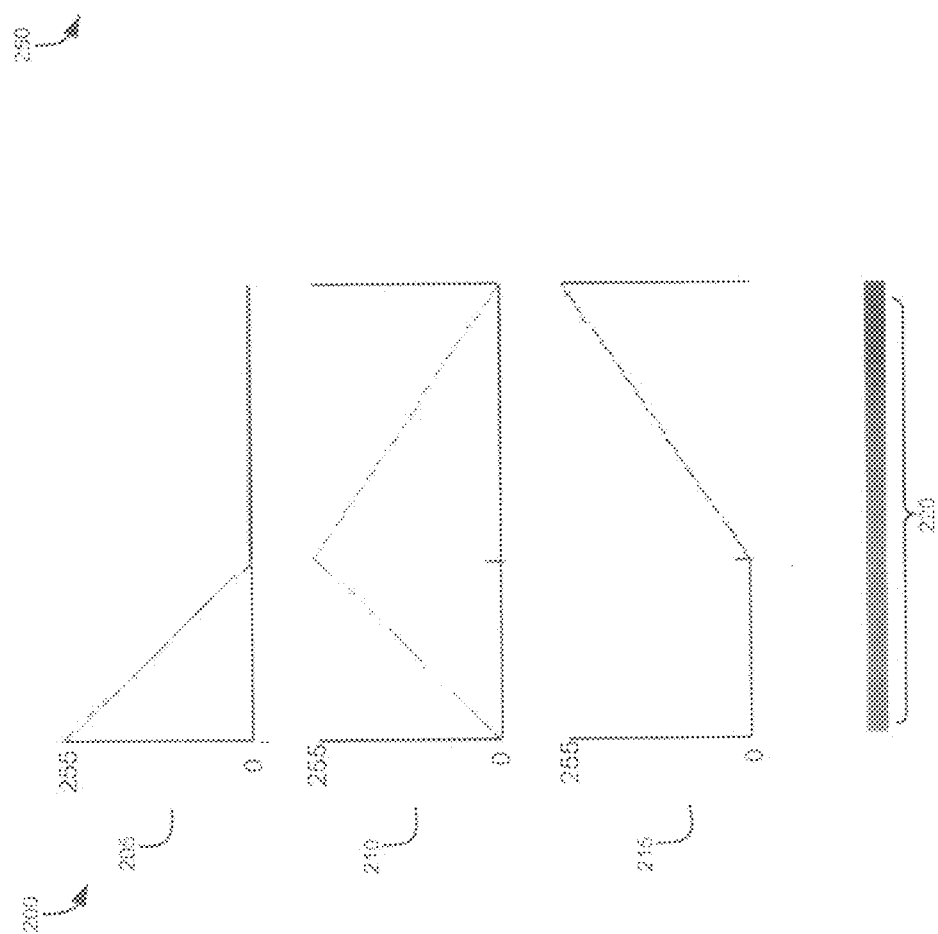
FIG. 2a is an example of a R, G and B color scale.

Referring to FIG. 2a, color scales 200 representing each of the R 205, G 210, and B 215 components in the RGB color space may be combined to form a spectrum of colors 220. Component values of other color systems, e.g. CIE L*a*b* and HLS, may also be combined to form a spectrum of colors, as known in the art. A value ranging from 0 to 255 of each R 205, G 210, and B 215 color components may be combined to form colors along the color scale 220. Thus, R, G, and B values combined represent a color along the color scale 220. Referring to FIG. 2b, an RGB color scale 250 may be illustrated wherein the R value 260 is saturated to the highest level (255). The R value may be nearly saturated particularly in images or specific pixels exhibiting a high degree of visible redness.

Figure 3:
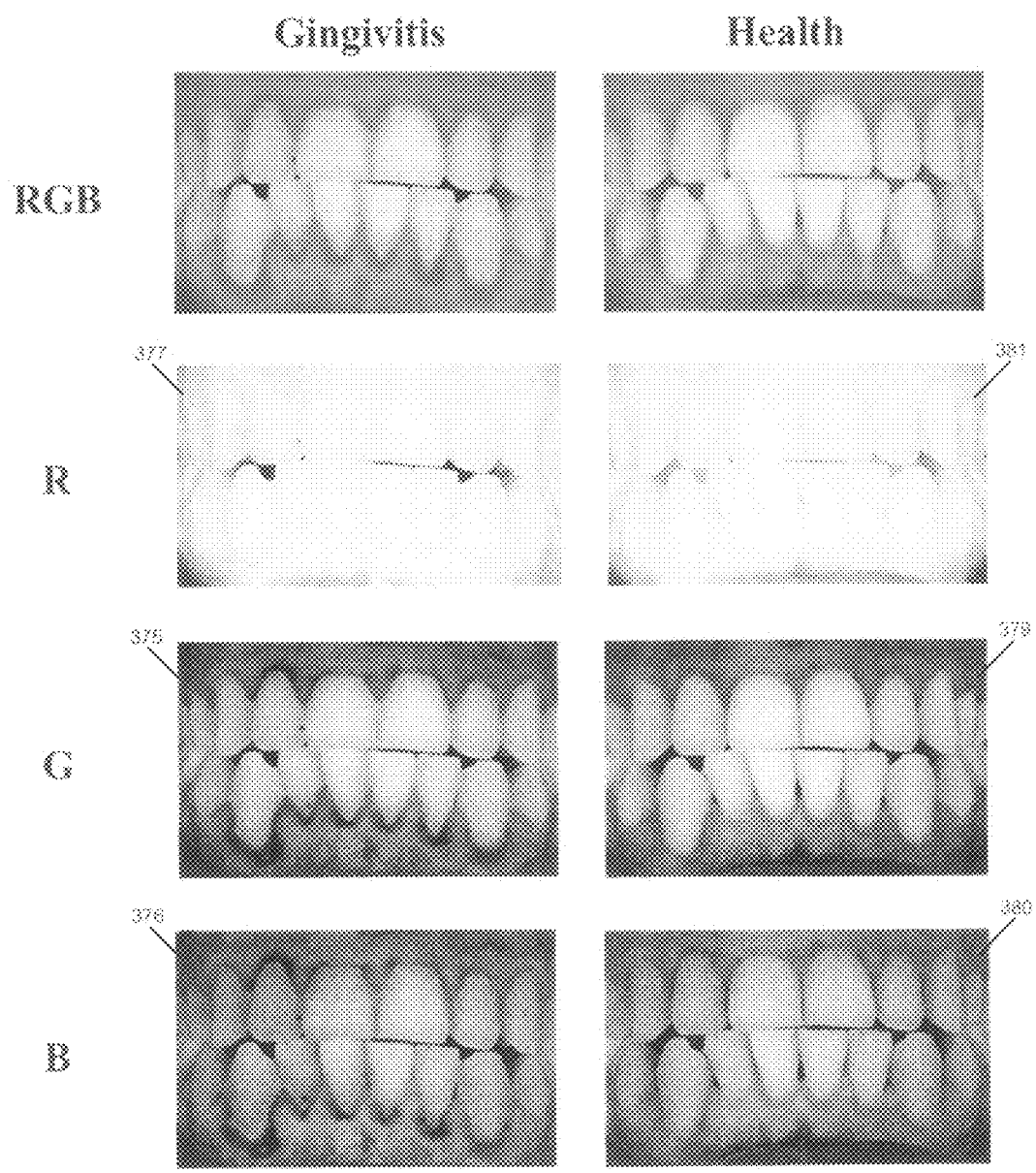
FIG. 3 is an example of healthy and diseased gingival tissue images, along with the corresponding R, G, and B component values in grey tones.

The degree to which an image or individual image regions present healthy or diseased tissues may be related to the degree of redness. For example, as shown in FIG. 3, diseased tissues 375, 377 may exhibit a higher degree of redness, as measured by either the G or B component color values, than healthy tissues 379, 381. While not intending to be bound by any theory, it is believed that the amount of "redness" can be characterized in one instance by the G, or B, component color values due to the absorption characteristics of blood, and more particularly hemoglobin, which is present in an increasing amount as tissue progresses from healthy to diseased, or due to other conditions which can lead to inflammation of the soft tissue. In an alternate arrangement, a change in redness can be measured by a multi-spectral imaging analysis of the green and/or blue wavelengths. In one embodiment, one or more wavelengths between about 380 nm and about 565 nm are measured. In another embodiment, one or more wavelengths between about 520 nm and about 565 nm are measured. In yet another embodiment, one or more wavelengths between about 435 nm and about 500 nm are measured. Other absorptive or reflective wavelengths can also be measured that are associated with other blood components (e.g., red cells, white cells, platelets, plasma, blood clotting factors, sugars, lipids, vitamins, minerals, hormones, enzymes, antibodies, bacteria, and proteins), biomarkers of inflammation (e.g., cytokines), soft tissue components, disease response, or disease conditions.

FIG. 3 illustrates, in gray tones, the R, G and B component values for healthy and diseased tissues. The gray tones signify the relative value of the R, G, and B components. For instance, the gray tones for the R component 377, 381 show less variation than the gray tones of the G 375, 379 and B 376, 380 components. Other color values can also be used to characterize the amount of redness where the color value/color characteristic is related to the spectral absorbance of blood or components such as hemoglobin, including, but not limited to, ratios of R, G and B component values (e.g., G/R and B/R), algorithms involving R, G and B component color values (e.g., 2R-B-G), and L* or a* in the LAB color space. R, G, and B component values will be discussed hereafter for simplicity.

Figure 4:
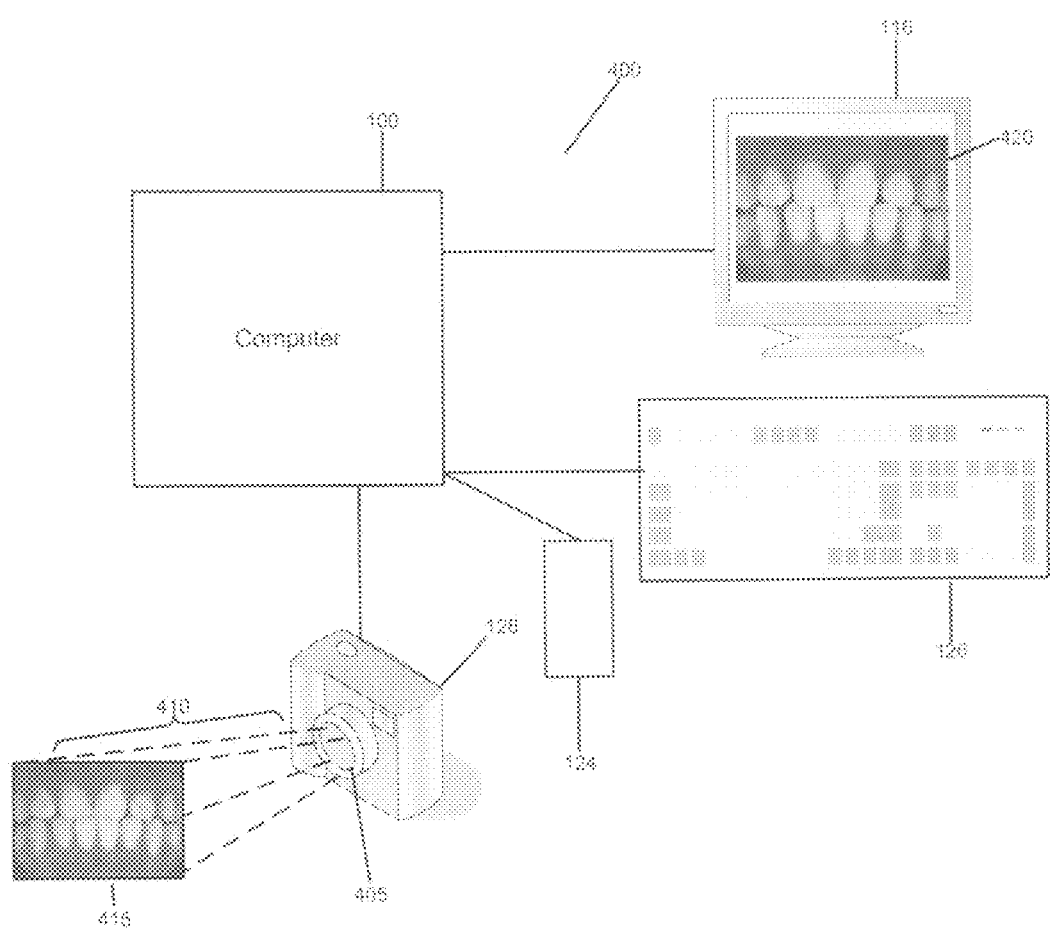
FIG. 4 is an example of a system for implementing the described method.

With reference to FIG. 1 and FIG. 4, an automated system 400 for analyzing gingival tissues may include a first input device in the form of a digital camera 128, a second input device in the form of a mouse 124, a third input device in the form of a keyboard 126, and a display 116. The digital camera 128 may be connected directly to the computer 100 for transferring images thereto or images may be stored on a portable computer readable medium which may be read by a device connected to the computer 100. The digital camera 128 may be configured to have a sensor 405, such as a Bayer Pattern Sensor or 3 CCD sensors such as those found in a 3-chip camera, that has an array of rows and columns of photosensitive detectors (such as a charge-coupled device or CCD) for detecting light 410 from an image 415. The captured image 415 may be any combination of the R, G, and B wavelengths (i.e., single- or multi-spectral). A processor within the digital camera 128 converts the output from the sensor 405 into a data file that records one or more color values associated with each photosensitive detector. The color value is typically a luminance value for one or more of R, G, and B values. The values may range between 0 and 255 for an 8-bit camera. A higher bit depth camera may be used, in which case the values may have a much greater range (e.g., a 12-bit camera has a range of 0 to 4,095).

With reference to FIG. 1, FIG. 2, FIG. 4, and FIG. 5, the display device 116 may display captured images 415 as any number of picture elements, or pixels 500. A pixel 500 of the display device 116 of the system 400 may display a color based upon the R, G, and B color values recorded from the digital camera 128, to reproduce the captured image 415 as a displayed image 420 on the display 116. For example, the camera 128 may record and the computer 100 may display values of 255 for R, 128 for G and 128 for B for the pixel 500. The color values can be stored in a variety of digital file formats, including Joint Photography Experts Group standard (JPEG) and Tagged Image File Format (TIFF). Other file formats may be used as known in the art. The position of the pixel 500 within the displayed image 220 and the display 116 may also be recorded on the computer system 400. The position of the pixel 500 may be expressed as a set of coordinates, x and y, for example, where "x" may represent the pixel 500 position along a horizontal axis and "y" may represent the pixel 500 position along a vertical axis. The pixel's 500 RGB values and position may be stored on the system 400. While a digital camera is illustrated, it may be appreciated that an analog camera may also record images on film. The film images may then be scanned by a scanner 130 connected to the computer 100 and the images recorded on a computer readable medium connected to the system 400.

Referring to FIG. 1, FIG. 2, FIG. 4, FIG. 5, FIG. 6a-c, and FIG. 7, a method, which may be computer implemented, is illustrated. The method may comprise a plurality of operations for analyzing a gingival image and displaying the analysis results. The method may include any combination of the several operations as herein described. At 605, a camera 128 may create a captured image 415 of a subject's soft tissue(s). The soft tissues may include one or more of the marginal gingiva, gingival sulcus, inter dental gingiva, gingival gum structure on the lingual and buccal surfaces up to and including muco-gingival junction, and the palate. The gingival tissues may include tissues of the maxillary and/or mandibular arches and may also include soft tissue adjacent one or more of (or portions of) the incisors (central and/or lateral) and canines of the maxillary and/or mandibular arches, bicuspids, molars and edentulous spaces or sites adjacent to implants or other fixed or removable prostheses. Instruments, such as retractors, may be employed to expose the desired portion of the soft tissue for an image capture and analysis.

A captured image 415 may be obtained with a digital camera 128 under controlled lighting conditions. An example of a digital camera 128 may be the Finepix™ S2-Pro as produced by Fuji Photo Film Co., Ltd., of Tokyo, Japan. The camera 128 may be of suitable resolution for capturing color gradations, particularly the color variances in gingival tissues. For example, a digital resolution of 800×600 pixels may be suitable. Further, the digital camera 128 may be able to obtain captured images 415 in a selected one of the R, G, or B color wavelengths, or may be a multi-spectral camera. The camera 128 may also be configured with a linear polarizing lens 417 that may capture cross-polarized light, or any other lens that may reduce the amount of glare or other light interference received at the camera 128. An example of a suitable lens may be the Micro Nikkor lens with a linear polarizing filter produced by Nikon Corp. of Tokyo, Japan. A standard, fixed set-up may be used to ensure reproducible conditions with respect to light-subject-camera geometry. A digital camera 128 may be mounted a fixed distance away from a cup-type chin rest with lights positioned on each side of the camera 128. The body of the camera may be a distance from the front of the chin rest. Dedo™ lights of the type produced by Dedotec, USA, Inc. of Cedar Grove, N.J. may be mounted on each side of the camera 128 and equipped with a series of filters. Each light may be positioned a distance from the system centerline. The lights may also be placed at an angle relative to the centerline of the system. The light filters may be a heat shield, a polarizer, and a bluing filter. The heat shield may serve as a comfort measure for the subjects, the polarizer may provide polarized light to the tooth surfaces, and the bluing filter may raise color temperature. The filters may be attached to the front of the lights using a custom mounting bracket that positions the filters a distance from the front of the light lens. Each Dedo™ light may be fitted with a suitable bulb, for example, the Xenophot™ type, 150 W, 24V as produced by Sylvania of Danvers, Mass. The bulb may be powered with a tunable voltage power supply and powered in series. The slideable bulb socket of the Dedo™ light may be positioned at the back of the light housing and locked down. A power supply equipped with a rheostat may be used to set the voltage to approximately 46V. A difference between the series bulb voltage and initial set-point may protect against accidental overpowering of the bulbs and may provide adjustment latitude during calibration and standardization. The camera 128 may obtain a captured image 415 in a setting configured to eliminate any extraneous light from windows or other light sources. For example, the only light in the room may be provided by the imaging system light sources. The system may be placed a distance away from camera-visible walls, such that, the camera may not detect light reflected off of the walls.

A zoom lens may be attached to the camera 128 for better imaging. The lens may be a 4×75 mm type lens as produced by Fujinon Corp. of Saitama, Japan. The focal plane of the lens may be set a distance from the lens and the lens may be locked down to prevent adjustments. A polarizer may be added to the zoom lens and rotated to a position of cross polarization relative to the light polarizer. The cross polarization may be set by placing a chrome ball or other reflecting surface at the focal plane and rotating the polarizer on the lens until the glare spots on the reflecting surface disappear. A suitably-sized chrome ball may be approximately 19 mm in diameter. This combination of lighting, camera and lens settings may produce RGB values of approximately equal and not saturated for a pure white sample, to assure that the camera may not be saturated on any of the color channels.

The height of the chin rest may be mounted such that the floor of the chin rest may be a distance from a support surface. Other fixation may be used, such as a forehead rest. Images may be captured without any fixation. Similarly, the bottom of the camera base may be a distance from the support surface. The camera 128 may be controlled by a general purpose computer 100. One example of a general purpose computer may be produced by Dell, Inc. of Round Rock, Tex.

While in use, the system 400 may be black/white balanced and standardized to two color reference standards. The black balance may be established by putting the lens cover on and capturing an image 415. The black balance may be adjusted until uniformity is achieved across the R, G and B channel. A gray reference standard image in the focal plane may then be captured and the white balance adjusted to bring the color channel values to uniformity across R, G and B channels. After white balancing, a second image of the gray standard may be captured. The gray value of each pixel may be normalized to the mean intensity of the image to generate a position dependant ratio correction for any variations in lighting intensity across the field of view of the camera. This intensity correction may be applied to each subsequently captured image.

An image of a color standard may be captured as a separate image or as part of an image of the oral cavity. The average R, G and B values of each color may be extracted and compared to a standard set of values which serve as the standardization point for the camera 128. These standardization values may be determined by using several cameras to capture images under the conditions established with the system 400. If the R, G and B values are within pre-established tolerance values, then no further system 400 adjustment may be needed. If the values are outside tolerances, the system 400 may be adjusted. For example, the light intensity may be adjusted to bring the system 400 within the tolerances. To color correct for inevitable remaining differences between the captured values and the standard values, a polynomial color correction may be established by regressing the standard values for each channel against the captured values including the cross channel terms where:

Rcorrected=f(Rinput, Ginput, Binput);
Gcorrected=f(Rinput, Ginput, Binput); and
Bcorrected=f(Rinput, Ginput, Binput).

The system 400 may be color calibrated approximately every hour during use or more frequently as needed. After successful standardization, the position dependent intensity correction and the color correction may be applied to each subsequently captured image until the next calibration cycle. If a color standard is captured in each image, standardization may be performed separately for each image. Each calibration set including raw values and calibration results may be written to a text file each time the system is calibrated. A complete system 400 calibration to include, but not limited to, light standardization, light-camera-subject geometry, polarization calibration, black/white balance, and color standardization may be performed before daily use.

A subject may use cheek retractors such as those supplied by Salvin Dental Specialties of Charlotte, N.C. to pull the cheeks back and allow for unobstructed illumination of the gingival tissues. Prior to use, the clear retractors may be given a matte finish to avoid the possibility of depolarizing the light and producing glare in the captured image 415. Each subject may then put their chin in the rest, while the operator provides instructions to properly align the subject based on a live output view from the camera 128. The subjects may hold the maxillary 477 and mandibular 479 incisors tip to tip to avoid an overlap of the maxillary and mandibular teeth. The subjects may be instructed to look straight on to the camera 128 to avoid any left right rotation and forward or backward tilting of the head, and to pull retractors by the ends of the handles toward the ears to avoid any shadowing resulting from the retractors or the subject's hands. Retractors may also be of a one-piece design that may expose the desired area of gingival tissue automatically without the subject's involvement. The subject may also retract the tongue away from the teeth. If excess saliva is observed, the subject may remove the retractors, close their mouth to clear the saliva before repositioning. When in position, the image 415 may be captured, processed through the intensity and color correction, and saved to the system 400.

Figure 5:
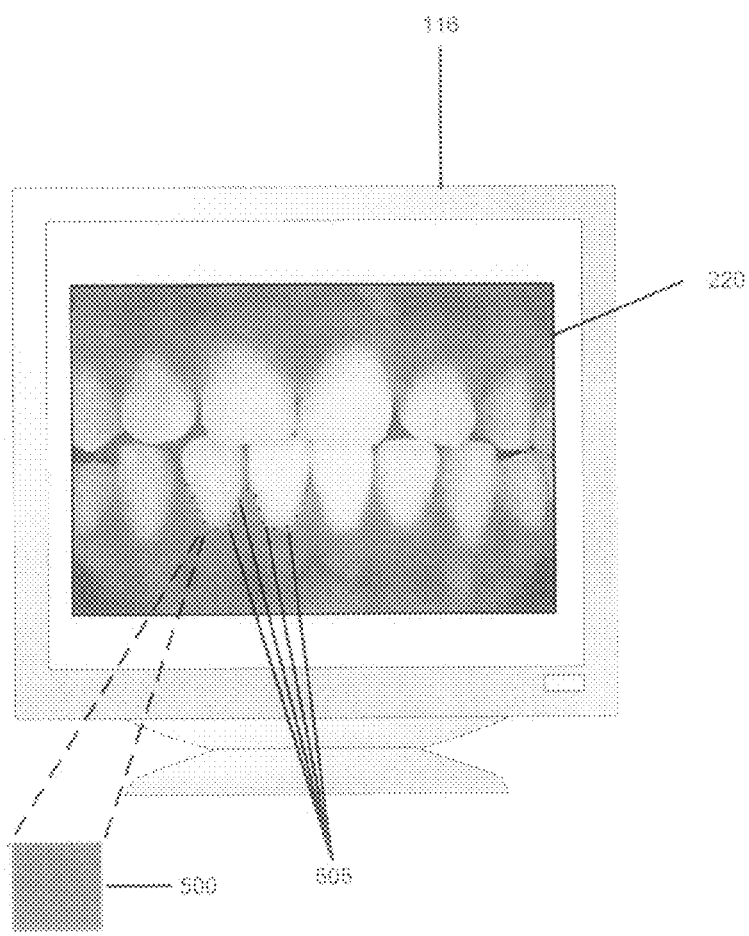
FIG. 5 is an example of a gingival tissue image and display.
Figure 6:
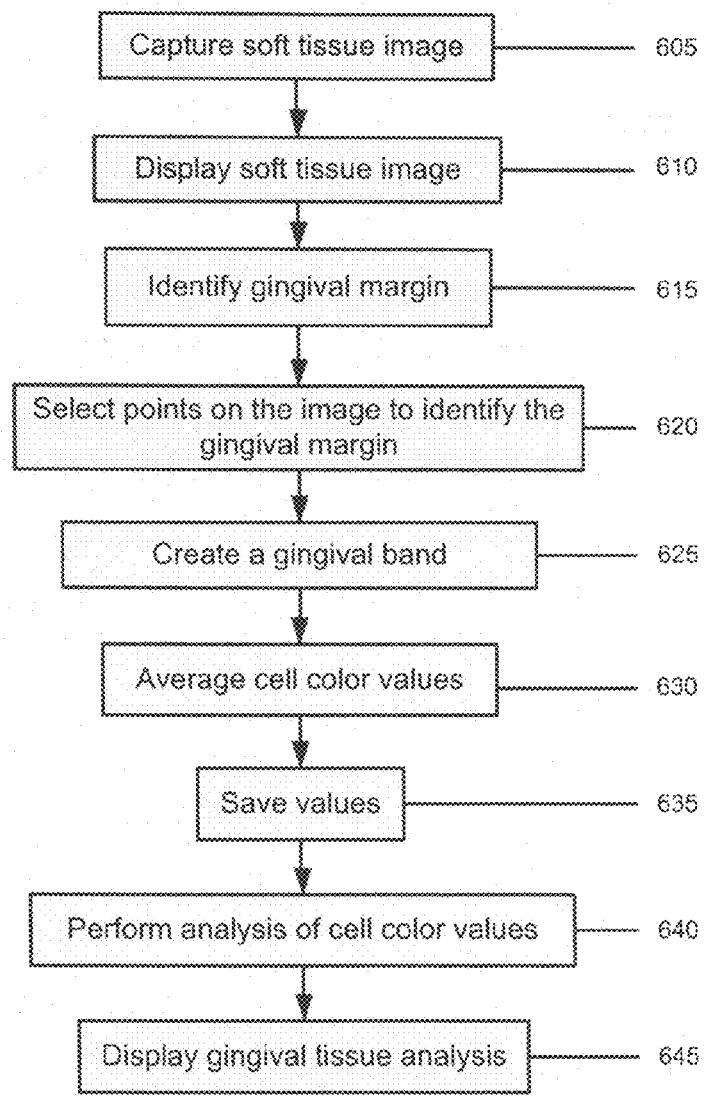
FIG. 6 is a flowchart describing a method of one example of using the system of FIG. 4 to analyze gingival tissues.

Referring to FIG. 6, at 610, the captured image 415 from 605 may be transferred to the display 116 to become a displayed image 420 of the system 400 as, for example, in FIG. 4 and FIG. 5.

At 615, a gingival margin may be identified. As used herein, the gingival margin may be an edge of the soft tissue (i.e., the boundary at the end or edge of the soft tissue and the hard tissue) or may be a selected boundary that is near, adjacent to, or close to the edge of the soft tissue. The gingival margin may also be some distance from the edge of the soft tissue and the location of the boundary may vary depending on the type of analysis desired.

Figure 7C:
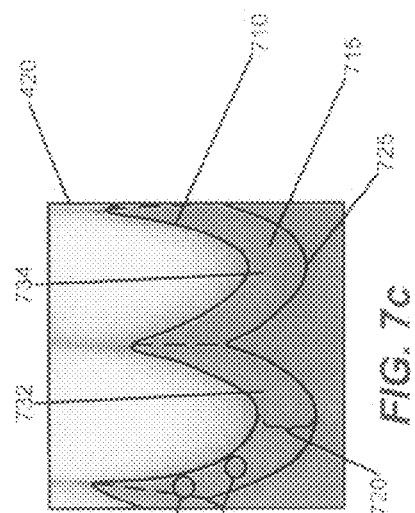
FIG. 7c is an example of a gingival tissue image and a selected gingival band.
Figure 7B:
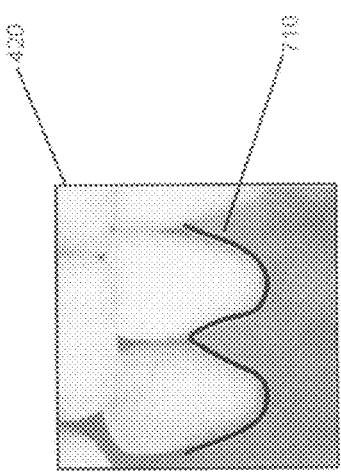
FIG. 7b is an example of a gingival tissue image and a selected gingival margin.
Figure 7A:
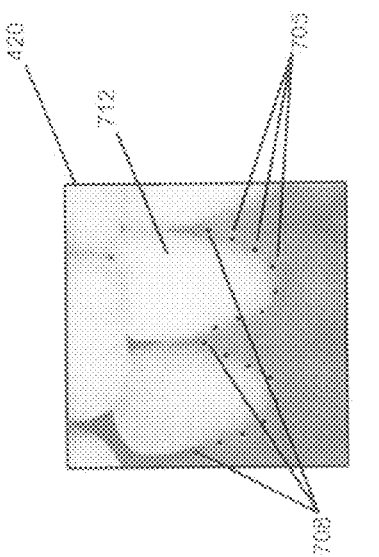
FIG. 7a is an example of a gingival tissue image and a plurality of selected analysis points.
Figure 8:
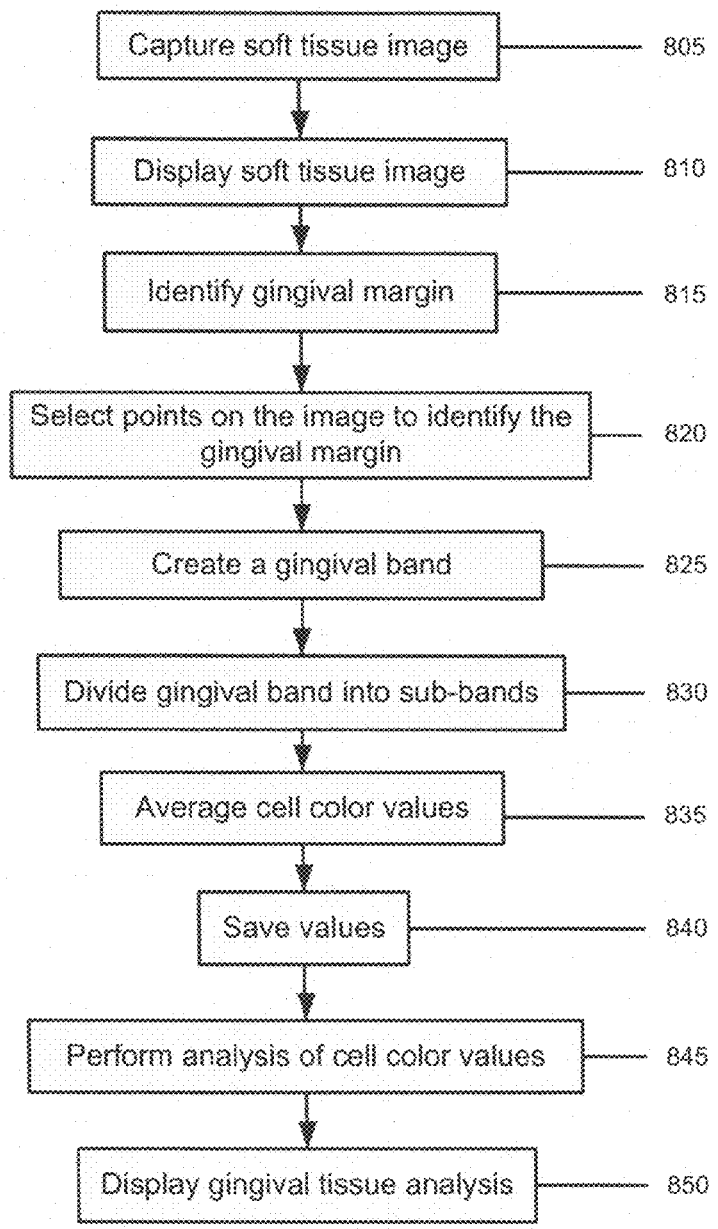
FIG. 8 is a flowchart describing a another method of using the system of FIG. 4 to analyze gingival tissues.

With reference to FIG. 7a, at 620, a series of points 705 on the displayed image 420 may be selected to identify the gingival margin for analysis. Points 705 may be selected to measure the color of the gingiva while selecting as few of the pixels 500 representing the tooth as possible. As used herein, a tooth may be any naturally hard structure found in the jaws and used for chewing, or any man-made material representing a tooth such as, but not limited to, crowns, caps, dentures, partial dentures, dental implants, bridges, and the like. Points 705 may be selected using a mouse 124, any suitable pointing device, or the keyboard 126. Also, the display 126 may be modified to include a sensor configured to discern the selection of points 705 on the displayed image 420. Each point 705 may be a pixel 500 and may be stored within a memory component of the computer 100 as a coordinate. Pixel coordinates 705 may be identified separately for each arch (maxillary, mandibular) moving left to right across the displayed image 420. The pixel coordinates 705 may be chosen to be close enough together so that interpolating between them may allow for accurate definition of a gingival margin 710. For example, approximately one hundred pixels may be selected per arch per displayed image 420 under a camera resolution of approximately 45 pixels per millimeter. A suitable and readily-available computer application such as the ImageJ freeware application may be used to identify the pixel coordinates 705. Other information may also be collected and saved with the data representing the pixel coordinates 705 such as a time or type of visit prompting the analysis, an indication of whether the data represents an analysis of the mandibular or maxillary arch, an indication of the order in which each pixel coordinate 705 was selected, and an indication of the physical location of the pixel 705 in the displayed image 420. Papilla pixel coordinates 708 selected from the displayed image 420 may also represent the pixels at the tips of the papilla. The area between the papilla pixel coordinates 708 may further define a region of the gingival margin 710 associated with a tooth 712. Any number of pixel coordinates 705, 708 may be selected. For example, approximately 15 to 25 pixel coordinates 705, 708 may be selected per tooth, though more may be chosen. Further, the number of teeth may be increased and may depend on the curvature of the subject's dental arches. Also, any range of teeth from any region of the subject's mouth may be selected and images 420 selected from different angles of the mouth. Lingual surfaces may also be selected and points chosen.

With reference to FIG. 7b, a line 710 may be constructed through the pixel coordinates 705 using linear interpolation or any other tool known in the art for linking the pixel coordinates 705 in order to define the gingival margin 710.

With reference to FIG. 7c, at 625, the pixel coordinates 705, image data, and other measurements may be organized or arranged to define a gingival band 715. The gingival band 715 may have a width 720 that may identify a specific region of the gingiva. For example, the gingival margin 710 may define a first margin or boundary of the gingival band 715 while the gingival band boundary 725 opposite the gingival margin 710 may define a second boundary of the gingival band 715. The pixel coordinates 708 that identify the tips of the papilla of the gingival margin 710 may then define a region of the gingival band 715 associated with each tooth 712. The width 720 of the gingival band 715 may vary depending upon the type of analysis desired. For example, the width 720 of the gingival band 715 may vary between approximately 0.1 to 5 mm. In one embodiment, the width is between about 1.25 mm and about 1.5 mm. Additionally, the gingiva for more or different teeth may be selected, as well as the gingival from lingual gingiva. The gingival band 715 may be described as a region of interest for analysis. For the mandibular arch, the gingival margin 710 may define the upper edge of the region of interest. The lower edge of the region of interest may be the set of pixels 500 running the length of the gingival margin 710 that is a uniform proximity to the gingival margin. For example, for each horizontal coordinate (X) along the gingival margin 710, a vertical coordinate (Y) may be identified such that the shortest distance between the (X,Y) position and all the pixels on the gingival margin 710 is a set distance. The set distance may be within a range of 0.1 to 5 mm. The set of (X,Y) coordinates that satisfy this criteria may define the lower boundary 725 of the region of interest for the mandibular arch. Maxillary arch calculations follow the same process, though the upper/lower orientation is reversed. All calculations and analyses may be performed using the Statistical Analysis System (SAS) as produced by SAS Institute Inc. of Cary, N.C. At 630, color values of the pixels, consisting of a value of each R, G, B color component, within the gingival band 715 may be mathematically manipulated and analyzed for patterns and trends that may permit the matching of a diagnosis. For example, the color values of the pixels within the gingival band 715 may be averaged to calculate one or more color values for the band 715. The pixels may be grouped into cells so and the color values for that grouping or cell may be averaged or otherwise mathematically manipulated. The regions or cells can have a variety of shapes and/or sizes, depending upon the desired analysis. The values for the pixels within a cell so averaged or manipulated are referred to herein as cell values. Alternatively, the color values for the pixels of the entire band 715 may be averaged. Results may be calculated separately by arch (maxillary, mandibular) or both arches may be combined. An example for a region or cell 727 of the band 715 containing 10 pixels where the pixels within the cell have been averaged is set forth below in Table 1.

TABLE 1

| Pixel (x, y) | R Value | G Value | B Value |
| --- | --- | --- | --- |
| (1, 1) | 149 | 125 | 118 |
| (2, 1) | 149 | 125 | 118 |
| (3, 1) | 146 | 128 | 116 |
| (4, 1) | 145 | 127 | 115 |
| (5, 1) | 145 | 127 | 115 |
| (6, 1) | 145 | 127 | 115 |
| (7, 1) | 146 | 127 | 115 |
| (8, 1) | 147 | 128 | 116 |
| (9, 1) | 147 | 130 | 115 |
| (10, 1) | 147 | 130 | 115 |
| Average Cell Values | 147 | 126 | 116 |

The average color values for several regions or cells 727, 730, the entire gingival band 715, or any portion of the gingival band 715 may be similarly averaged or mathematically manipulated. For instance, regions 727 and 730 may be selected according to user preference, for example, if the user determines that the regions 727 and 730 should be examined more closely. Other regions 732, 734 may be selected as related to a particular tooth as define by the papilla pixel coordinates 708. The color values for a plurality of cells or regions may be averaged to determine representative color value for the entire band 715 or a subset thereof, such as a plurality of regions or cells. An example for a band 715 containing 6 regions whose values have been averaged to determine composite R, G, and B values for the band is set forth below in Table 2.

TABLE 2

| Region | R Average | G Average | B Average |
| --- | --- | --- | --- |
| #1 | 149 | 125 | 118 |
| #2 | 149 | 125 | 118 |
| #3 | 147 | 128 | 116 |

TABLE 2-continued

| Region | R Average | G Average | B Average |
|---|---|---|---|
| #4 | 147 | 127 | 115 |
| #5 | 146 | 127 | 115 |
| #6 | 145 | 127 | 115 |
| Average Band Values | 147 | 126 | 116 |

At 635, the averaged values from 630 may be saved to a computer-readable medium either on the system 400 or sent to a network computer 156 and stored for archival purposes or further processing.

At 640, the computer 100 may perform several analyses on the data collected at 630.

At 645, the system 400 may display data, statistics, and images related to the analysis of 640.

With reference to FIG. 1, FIG. 4, FIG. 6, FIG. 8, and FIG. 9, another method, which may be computer implemented, is illustrated. The method may comprise a plurality of steps for analyzing a gingival image and displaying the analysis results. The method may include any combination of the several processes as herein described in any suitable order. As previously described in relation to FIG. 6, at 805, a camera 128 may obtain a captured image 415 of a portion of a subject's soft tissue(s). At 810, the data from the image capture 805 may be displayed on the display 116 of the computer system 400. At 815, a gingival margin may be identified. With reference to FIG. 9a and FIG. 9b, at 820, a series of points 905 on the displayed image 420 may be selected to identify the gingival margin 910 for analysis. With reference to FIG. 9c, at 825, a gingival band 915 may be created.

Figure 9A:
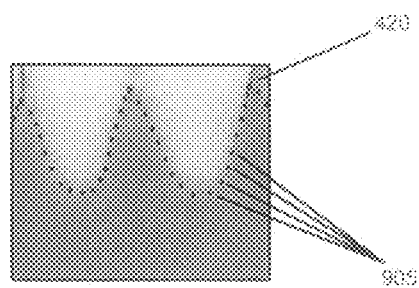
FIG. 9a is an example of a gingival tissue image and a plurality of selected analysis points.
Figure 9B:
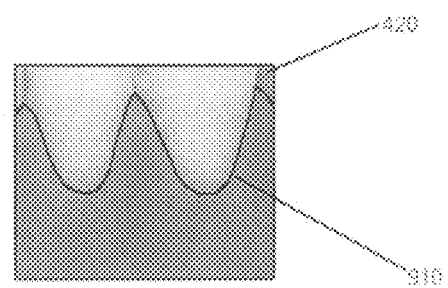
FIG. 9b is an example of a gingival tissue image and a selected gingival margin.
Figure 9C:
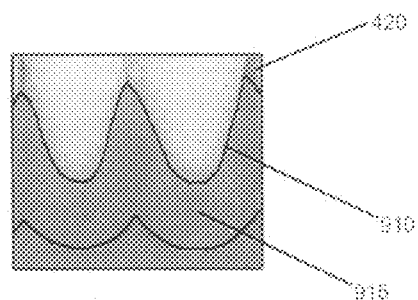
FIG. 9c is an example of a gingival tissue image and a selected gingival band.
Figure 9D:
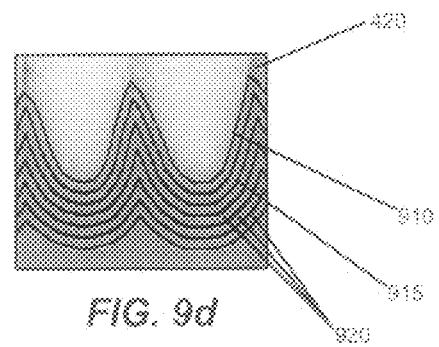
FIG. 9d is an example of a gingival tissue image and a selected gingival band divided into a plurality of sub-bands.
Figure 10:
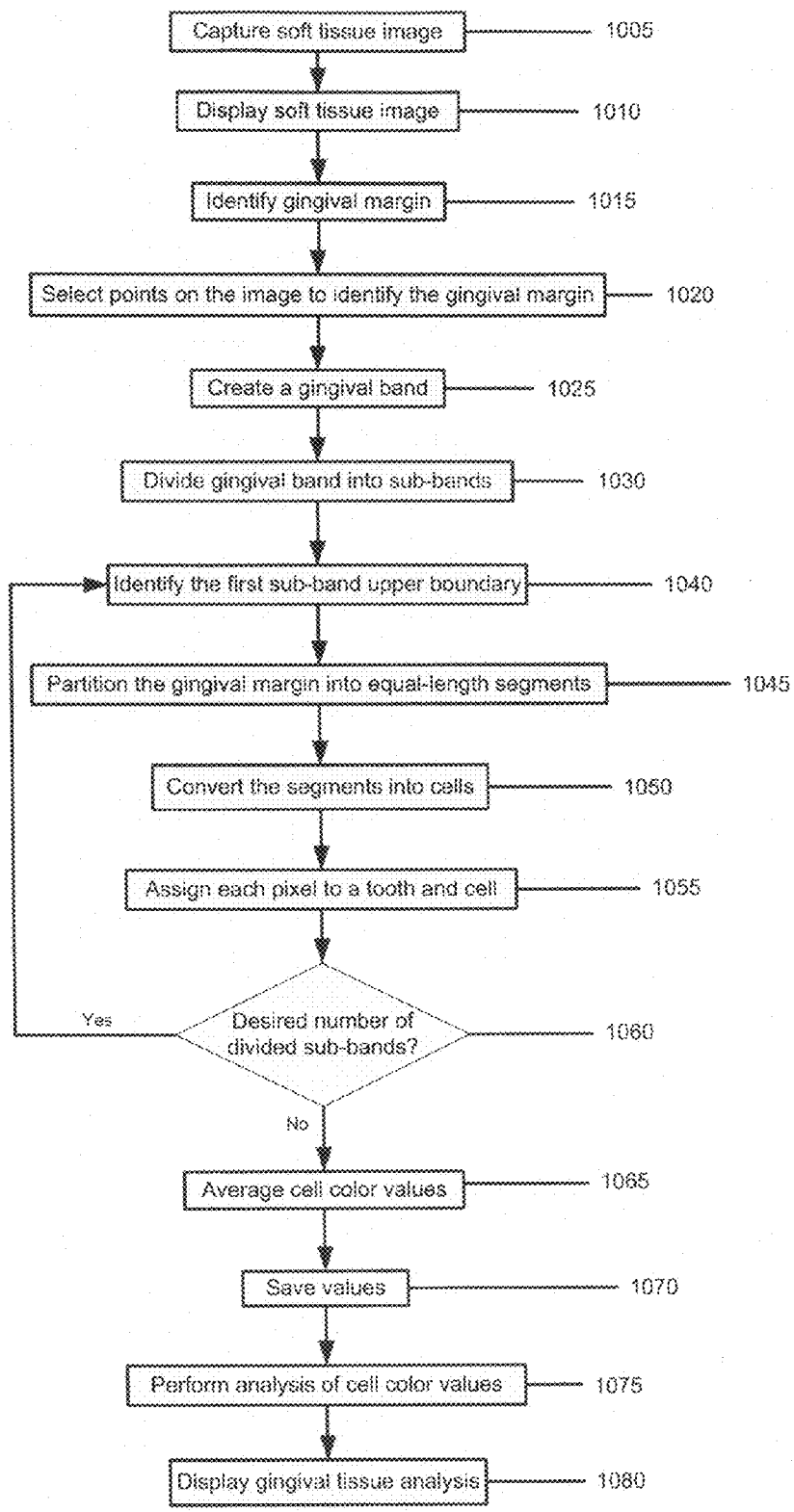
FIG. 10 is a flowchart describing yet another method of using the system of FIG. 4 to analyze gingival tissues.

With reference to FIG. 9d, at 830, the gingival band 915 may be sub-divided into a plurality of sub-bands 920 that extend mesially or distally along mandibular and/or maxillary arches. A sub-band may also be considered an elongated cell, or grouping of pixels, that merely extends in mesial or distal direction. The number of sub-bands created, however, may vary widely depending upon the desired analysis and the pixel size. In one embodiment, between about 8 and about 12 sub-bands 920 may be created. The sub-bands may have varying, uniform or dissimilar width. For example, the width of each sub-band 920 may vary between 1 and 50 pixels. Lines defining a boundary between each sub-band 920 may be created in a manner similar to the gingival band 915 creation of 825. The lines may be, but need not be, approximately parallel to the gingival margin 910.

At 835, color values of the pixels, consisting of a value of each R, G and B color component, within the gingival band 915 may be mathematically manipulated and analyzed for patterns, trends, diagnosis, and the like. For example, the color value averages as described in relation to 630 may be calculated for any part of the gingival band 915, for example, each sub-band 920. The average value for each sub-band 920 may then be combined to create an average for the entire gingival band 915 or each sub-band 920 average may be separated for later, individual analysis. At 840, the averaged values from 835 may be saved to a computer-readable medium either on the system 400 or sent to another computer 100 and stored for archival purposes or further processing. At 845, the system 400 may perform several analyses on the data saved at 840. At 850, the system 400 may display data, statistics, and images related to the analysis of 845.

With reference to FIG. 1, FIG. 4, FIG. 6, FIG. 10, and FIG. 11, yet another method, which may be computer implemented, is illustrated. The method may comprise a plurality of steps for analyzing a gingival image and displaying the analysis results. The method may include any combination of the several processes as herein described in any suitable order. As with the steps previously described in association with FIG. 6, at 1005, a camera 128 may obtain a captured image 415 of a portion of a subject's soft tissue(s). At 1010, the data from the image capture 1005 may be displayed on the display 116 of the computer system 400. At 1015, a gingival margin may be identified. With reference to FIG. 11a and FIG. 11b, at 1020, a series of points 1105 on the displayed image 420 may be selected to identify the gingival margin 1110 for analysis. With reference to FIG. 11c, at 1025, a gingival band 1115 may be created. With reference to FIG. 11d, at 1030, the gingival band 1115 may be sub-divided into a plurality of sub-bands 1120.

With reference to FIG. 11e-h, one or more sub-bands 1120 may be sub-divided into a grid of cells 1135. Steps 1040 through 1060 may be substituted or performed in combination with the creation of the gingival sub-bands, 830, 1030 described above. While the following steps describe the process as performed on the mandibular arch, it may be performed on the maxillary arch as well. The cells 1135 may have a variety of shapes and sizes. The cells 1135 may be uniform in shape and/or size or may vary from cell to cell. In one embodiment, they may be approximately rectangular and have a length and/or width determined by the width and contour of the tooth. For example, a computer program written using the SAS software product may divide the sub-bands 1120 into cells 1135.

Figure 11A:
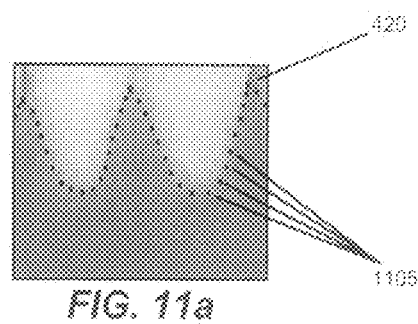
FIG. 11a is an example of a gingival tissue image and a plurality of selected analysis points.
Figure 11B:
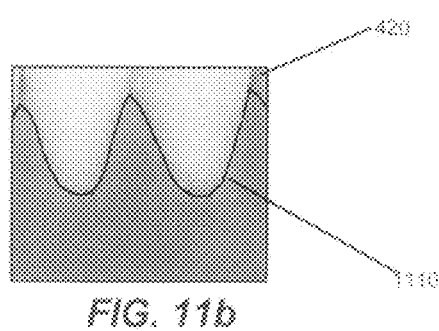
FIG. 11b is an example of a gingival tissue image and a selected gingival margin.
Figure 11C:
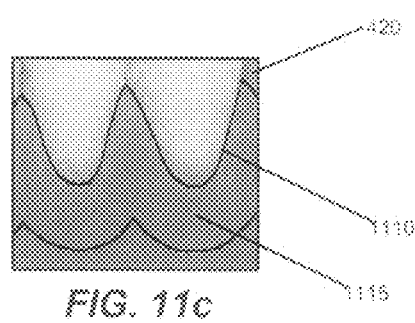
FIG. 11c is an example of a gingival tissue image and a selected gingival band.
Figure 11D:
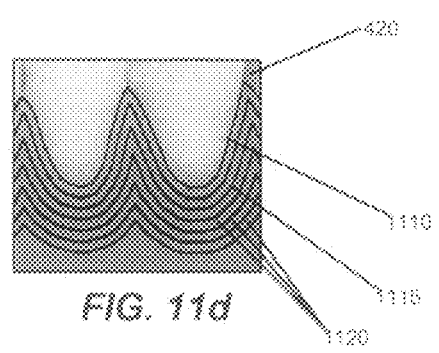
FIG. 11d is an example of a gingival tissue image and a selected gingival band divided into a plurality of sub-bands.
Figure 11E:
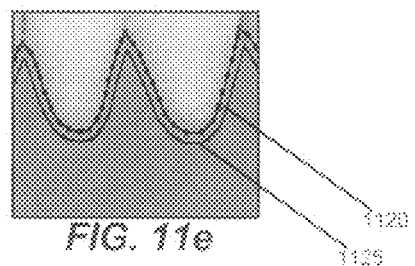
FIG. 11e is an example of a selected gingival margin and a gingival margin lower boundary.

With reference to FIG. 11e, at 1040, the lower boundary 1125 for a first sub-band 1120 may be identified. The lower boundary 1125 may be defined as the set of points with a minimum distance of approximately 'd' pixels from the gingival margin 1110. On the mandibular arch, these points may be on or below the gingival margin 1110. The collection of all pixels between the upper and lower boundary may become the sub-band 1120.

Figure 11F:
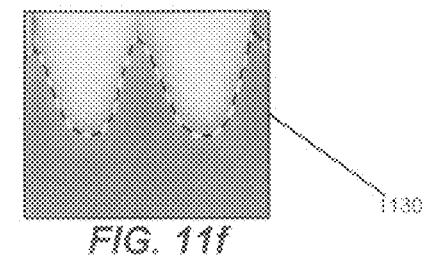
FIG. 11f is an example of a gingival margin divided into a plurality of lengths.

With reference to FIG. 11f, at 1045, the gingival margin 1110 may be partitioned into equal-length segments 1130. The number of segments 1130 per tooth may be equal or, if individual tooth analysis is desired, the number of segments 1130 may be different for each tooth. Further, if only a portion of the tooth is presented for analysis, the gingival margin 1110 may be broken into a number of segments 1130 equal to the fraction of the tooth shown in the displayed image 420.

Figure 11G:
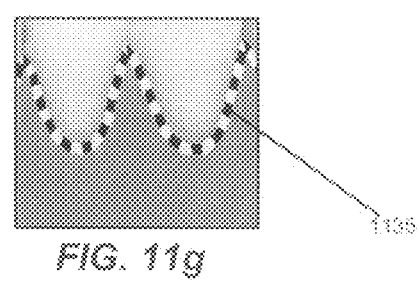
FIG. 11g is an example of a sub-band divided into a plurality of cells.

With reference to FIG. 11g, at 1050, each equal-length segment 1130 created at 1045 may be converted into a cell 1135 having a length equal to the equal-length segment 1130 and a height equal to the distance d. At 1055, each pixel in the sub-band 1120 may be assigned to the cell 1135 that contains it. The height of each sub-band may be between about 0.1 mm to about 1 mm. The cells may have length between about 0.1 mm to about 1 mm. The cells may contain between about 1 and 10,000 pixels or such other number of pixels as technology may allow.

Figure 11H:
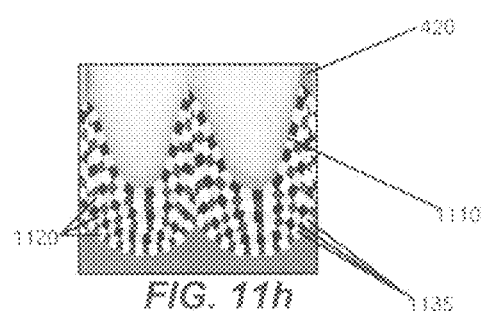
FIG. 11h is an example of a plurality of sub-bands divided into a plurality of cells.

With reference to FIG. 11h, at 1060, if the desired number of sub-bands 1120 are divided into cells 1135, the color values of the pixels (consisting of a value of each R, G and B color component within the sub-band 1120 or cell 1135) may be mathematically manipulated and analyzed for patterns, trends, diagnosis, and the like at 1065. For example, the color value averages as described in relation to 630 may be calculated. The average may be calculated for any part of the gingival band 1115, for example, each cell 1135, a portion of a sub-band, an entire sub-band, or the entire band 1115. For instance, the average value for each cell 1135 may be combined to create an average for the entire gingival band 1115 or each cell 1135 average may be separated for local analysis. If, at 1060, the desired number of sub-bands 1120 are not divided into cells 1135, the process may repeat beginning at 1040. At 1070, the averaged values from 1060 may be saved to a computer-readable medium either on the system 400 or sent to another computer 100 and stored for archival purposes or further processing. At 1075, the system 400 may perform several analyses on the data collected and saved at 1080. At 1080, the system 400 may display data, statistics, and images related to the analysis of 1075.

Figure 12A:
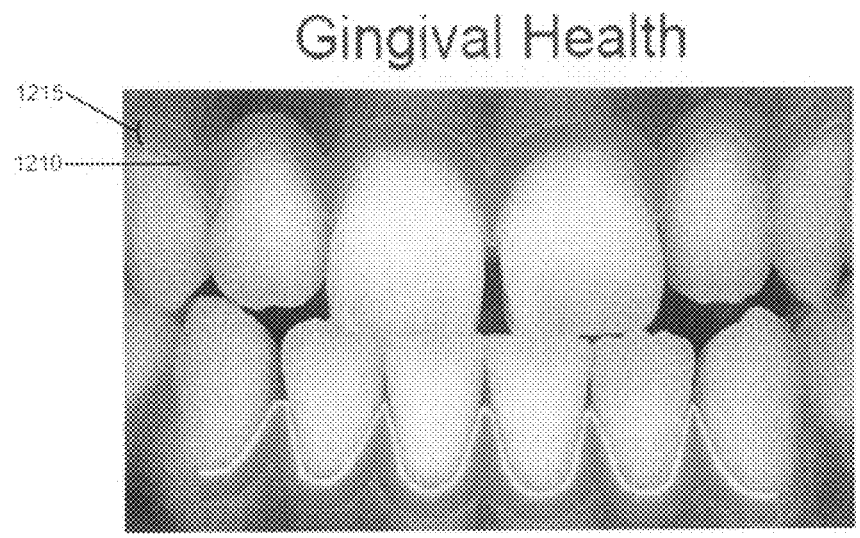
FIG. 12a is an example of an analysis performed on an image.
Figure 12B:
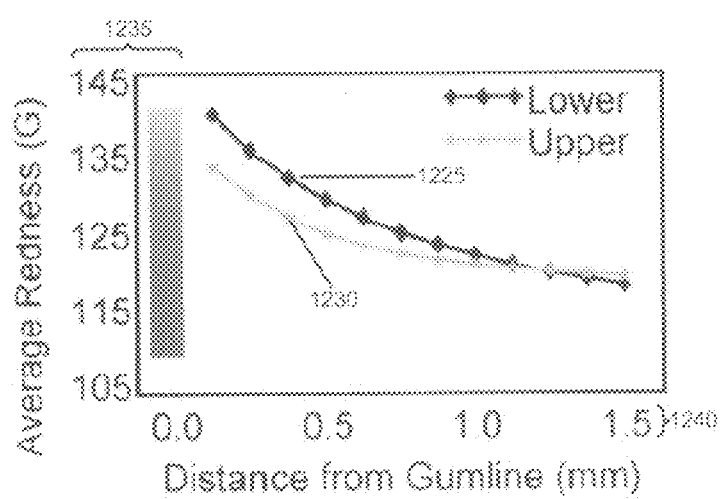
FIG. 12b is another example of a gingival analysis performed on an image.

Several different types of analyses may be performed on the data saved at 635, 840, and 1070. Each analysis may be performed alone or in combination with other types of analyses. With reference to FIG. 12*a* and FIG. 12*b*, for example, the homogeneity of the gingival color within a single image may be calculated. As used herein, homogeneity is intended to refer to the amount of color (e.g., "redness") variation (or lack thereof) within a region of interest. Homogeneity can be measured in variety of ways using a variety of color values and/or color characteristics. Healthy tissue may be light pink at the gingival margin 1210 and increase in redness with increasing distance from the gingival margin 1210. Therefore, redness homogeneity may be lower in healthy tissue. The onset of gingivitis may increase redness at the gingival margin 1210 and, therefore, result in higher redness homogeneity. The rate of change in gingival redness as a function of distance from the gingival margin 1215 may be calculated in the gingival band 1215 to quantify redness homogeneity. For example, the slope of a line representing G or G/R versus distance from the gingival margin 1215 as obtained by regression analysis of the region, sub-band, or cell data may be a suitable measure of color homogeneity. FIG. 12*b* provides a graphical representation of redness as a function of distance from the gingival margin. The homogeneity regression analysis may be represented as data taken from either the mandibular 1225 or maxillary 1230 arch. As shown in FIG. 12*b*, for healthy gingival tissue, the average value of 'G' 1235 may decrease as the distance 1240 from the gingival margin 1210 increases. The healthier the tissue, the higher the G value may be at the closest point to the gingival margin 1210.

Figure 13A:
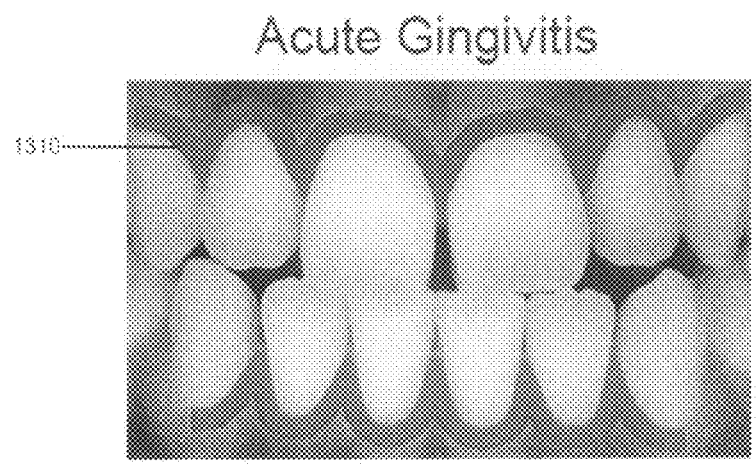
FIG. 13a is an example of a gingival analysis performed on an image.
Figure 13B:
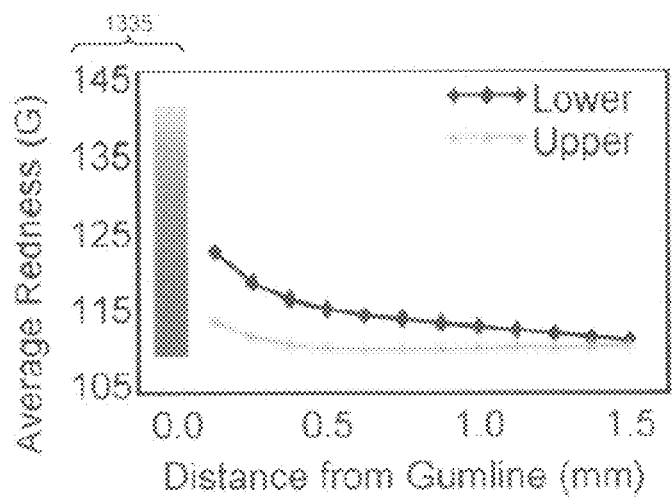
FIG. 13b is another example of a gingival analysis performed on an image.

In contrast, with reference to FIG. 12*a*, FIG. 13*a*, and FIG. 13*b*, diseased tissue may be more red as measured by a decrease in the G or G/R value of the image at the gingival margin 1310 as compared to the color of the healthy gingival margin 1210 of FIG. 12*a*. In addition to have lower G or G/R value, the redness versus distance from gingival margin slope of unhealthy tissue may be smaller and/or in opposite sign compared to healthy tissue. Therefore, an analysis of the redness present in gingival tissue versus the distance from the gingival margin may indicate the level of gingivitis.

In addition to displaying the change in redness versus distance graphically, as shown by way of example in FIGS. 12*b* and 13*b*, the change in redness versus distance within a single image can also be displayed pictorially. For instance, one or more display colors may be associated with one or more ranges of values for the slope of the lines 1225 and/or 1230 (or portions thereof) and the display colors may be displayed or superimposed on a mandibular and/or maxillary image or other display image to communicate the amount of homogeneity or heterogeneity of the redness of one or more regions of the gingival tissues of a subject. The image can be the image of a single subject within a study or clinical or may be a standardized image that used for all displays for consistency. The display colors can be superimposed over the regions of the mandibular or maxillary images that are associated with the calculated slope of the lines 1225 and/or 1230. This pictorial display could also be used to display the results for a group of subjects, where the slope of the lines 1225 and/or 1230 for a plurality of subjects are averaged together or otherwise statistically manipulated to arrive at a slope value representative of the plurality of subjects.

Further, at steps 635, 840, and 1070, an analysis of the gingival band 715, 915, 1115 color may be made on a region 727, 730 specific basis to compare the same relative location of gingival tissue for the same subjects between two different images 420. Values across sub-bands 920, 1120 may also be analyzed to generate a separate average value for each sub-band 920, 1120, either together or separately by arch. Further, values across cells 1135 may generate a separate average value for each cell, separately by arch. Within-subject comparisons may be made separately for each region 725, sub-band 920, 1120, or cell 1135. For example, a region 725, sub-band 920, 1120, or cell 1135 may be analyzed over time by statistically comparing the color average of several later images 420 (e.g. paired t-test, descriptive statistics, etc.). Statistical comparisons may be performed separately by arch or results may first be averaged across arches prior to statistical comparison.

Similarly, at 635, 840, and 1070, between-subject comparisons may be made on a site or region-specific basis to compare the same relative location of gingival tissue between two different subjects or groups of subjects. Between-subject comparisons may allow the evaluation of a hygiene regimen or product across a particular group. Further, the comparisons may be made against normative data. For example, averages of a region 727, 730 may result in a single average value of the endpoint per subject per arch. Averaging by sub-band 920, 1120 may generate a separate average value for each sub-band 920, 1120 separately by arch. Averaging by cell 1135 may generate a separate average value for each cell 1135 separately by arch. The subject-level average values may then be compared between groups using an appropriate statistical analysis method (e.g., descriptive statistics, analysis of covariance, etc). Analyses may be performed separately by arch or results may first be averaged across arches before comparing groups.

With reference to FIG. 6, FIG. 8, FIG. 10, FIG. 14, FIG. 15, and FIG. 16, at 645, 850, and 1080, the analysis data at 635, 840, and 1070 may be displayed or reported in a tabular format, a graphical format, or a pictoral format that superimposes color-coded results on a clinical photograph or other image, as previously discussed above. Within-subject results for one or the average result across more than one subject may be pictorially represented. For example, a range of colors 1410 associated with the change in redness 1415 over a period of time may be superimposed as a color-coded gingival margin 1420 on an image of one person's arches or a representation of more than one person's arches 1425. The color-code or color scale 1410 can be used to pictorially illustrate the amount of color change undergone by a subject, a group of subjects, or comparatively between subjects or groups of subjects. For example, the change in redness, as measured by a color value such as G, at a first location or distance from a gingival margin can be calculated at a plurality of points in time in a single (or plurality) regimen or clinical study (e.g., once a day or every 2, 3, 4, 5, 6, 7, 8, 9, 10, 14, 21, or 28 days or 2, 4, 6, 8, 10, or 12 months within a study).

A clinical study or trial is a research study in human volunteers to answer specific health questions. There are different kinds of clinical trials, including those to study: prevention options, new treatments or new ways to use existing treatments, new screening and diagnostic techniques, options for improving the quality of life for people who have serious medical conditions. Clinical trials are conducted according to a plan called a protocol. The protocol describes what types of patients may enter the study, schedules of tests and procedures, compositions, dosages, and length of study, as well as the outcomes that will be measured.

Figure 14:
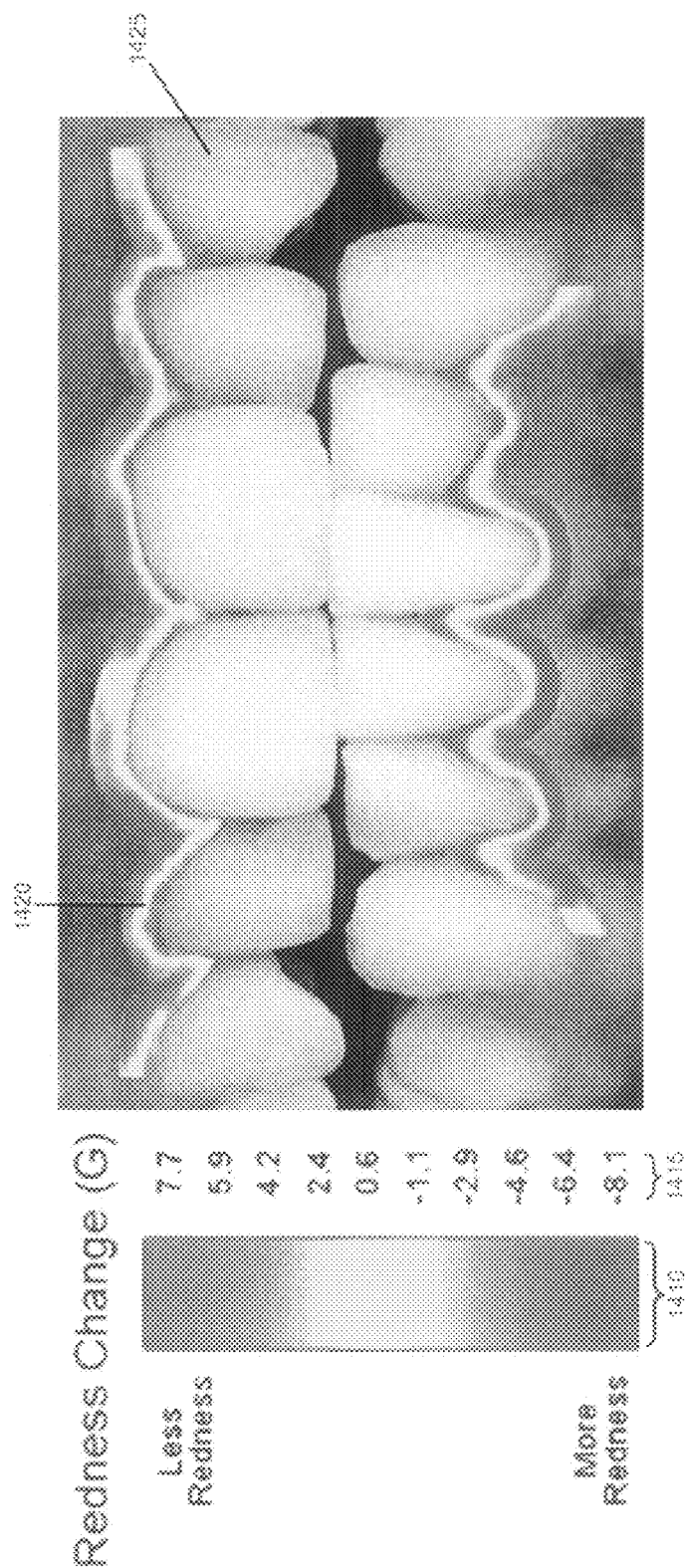
FIG. 14 is an example of a displayed result of gingival analysis.
Figure 15:
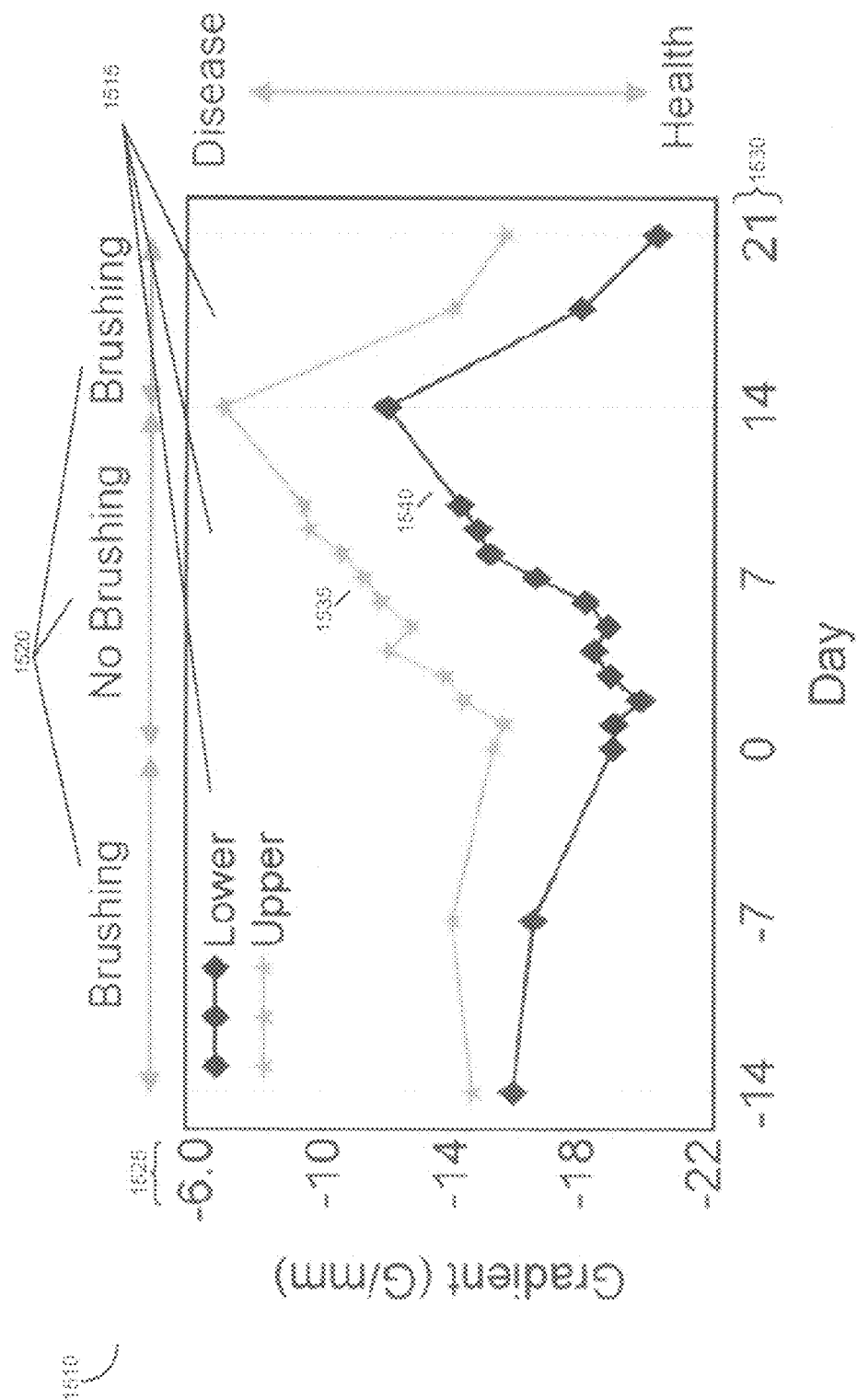
FIG. 15 is a graphical example of a displayed result of gingival analysis.

The change in redness between time points can be calculated by subtracting a first color value from a second color value to calculate a difference between the values. The difference can have a display color, such as a color from the range of colors 1410, associated therewith that can be superimposed on a maxillary or mandibular image, such as shown in FIG. 14, to communicate pictorially the change in gingival redness or the value of 'G'. For instance, in FIG. 14, the change in gingival redness or the value of G that occurred after two-weeks of no oral hygiene for 20 subjects or for a single subject who did not brush their teeth for 7 days but received professionally administered flossing may be illustrated by the differently-colored areas of FIG. 14. Other comparisons can be made. The change in redness can be with respect to a single subject, a group of subjects, for a single regimen or products, or a plurality of regimens or groups of products. Any mathematical values (including statistical values or any values derived from any algorithm) generated or calculated by comparing or manipulating color values from a plurality of images, plurality of subjects, plurality of regimens, or plurality of products is broadly referred to herein as comparison data. For instance, the change in redness between a first group of subjects and a second group of subjects can be made, wherein the first group might have used a first product or regimen and the second group might have used a second product or regimen. When a plurality of subjects are involved (or even for a single subject), the mathematical difference (or other mathematical values such as a sum, a ratio, etc.) in the color values for the subjects can be statistically manipulated (e.g., the differences for the plurality of subjects can be averaged or the variance, standard deviation, average deviation or mean absolute deviation, confidence interval, standard error, median, quartile, etc. can be calculated) to arrive at one or more representative statistically values that represents the plurality of subjects. The representative difference (or other statistical value) can be color-coded by having a display color associated with it and displaying the display color on a display image, as shown by way of example in FIG. 14. Further, the average change in gingival redness may be illustrated as a graph 1510, as shown by way of example in FIG. 15. The graph 1510 may be divided into different study periods 1515 in which different hygiene-related methods or products 1520 are used. The change or gradient of a color value from the gum line 1525 may be measured over a period 1530 between a subject or many subjects' upper 1535 and/or lower 1540 arches.

The average change in gingival redness may also be displayed in tabular form 1610, as shown by way of example in FIG. 16. Results may also be determined and displayed to compare the effects of different prophylaxis methods or regimens, different dental hygiene products or product combinations, demographic groups, or any combination of hygiene, products, prophylaxis, or demographic groups. Results may also be displayed as part of an advertising or marketing campaign to promote the effectiveness of a particular product or regimen.

The methods described above may be performed in a variety of settings for a variety of purposes. For example, the methods may be performed as part of a point of sale kiosk where a customer may try a dentifrice or other hygiene product for a period of time in order to determine its effectiveness. For example, the kiosk may contain a system for capturing an image of the customer's gingival tissues. The system may then analyze the image using any one or a combination of the methods as previously described. The system may then present the user with an analysis of his gingival tissues and include specific suggestions for suitable products to remedy any observed malady. For example, after analyzing the customer's gingival tissues, the kiosk may recommend a specific dental floss, dentifrice, powered or manual brush, rinse, adhesive, emollient or technique, or combinations thereof, to remedy the problem or potential problem. After trying the method or product for a period of time, the customer may return to the kiosk for another gingival tissue analysis. The system may then compare the results of the latest analysis with the previous analysis to determine the effectiveness of the product, technique, or regimen the customer used. A similar method may be employed to allow the customer to compare the effectiveness of competing products. The kiosk may also compare the individual customer's data with a repository of other customer data to provide further comparative information. The kiosks or any system as previously described to capture and analyze gingival tissue images may be distributed to allow the customer, a trained professional, or a technician to perform an analysis or comparison at many convenient locations. In addition to using the system and method in a point-of-sale setting, it may be used as part of a professional dental exam where the subject's gingival health may be determined as part of a periodic oral examination and comparisons are made between the condition or health of the tissue between dental visits. Further, the system may be employed as a mobile unit where technicians administer the test to subjects and provide an analysis without having to employ a trained professional to make an initial gingival health assessment.

The results of many analyses may also be used as marketing or advertising information to promote the effectiveness of particular products, combinations of products, and techniques. Examples of advertising claims that could be placed on product packaging that might be substantiated by the present invention include, but are not limited to, establishment claims (e.g., "clinically proven" or "tests show"), before and after claims (e.g., "10% less gingivitis after use"), monadic claims, comparative claims, factor-claims (e.g., "3× reduction in gingivitis"), and prevention and treatment claims. For example, product packages may refer to an analysis and demonstrate objectively-proven effectiveness or comparisons of the product. Also, analysis data may be used in clinical information related to different regimen that may or may not by used in combination with different products or groups of products.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

All documents cited herein are, in relevant part, incorporated herein by reference; the citation of any document is not to be construed as an admission that it is prior art with respect to the present invention.

It will be appreciated that any of the features, steps, or aspects of the present invention described herein may be combined, in whole or part, with any other feature, step, or aspect of the present invention described herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating oral cavity soft tissue of at least one subject, comprising:
    identifying a first gingival margin of at least one first gingival tissue image;
    creating a first gingival band, the first gingival band including the first gingival margin and a first ending boundary;
    dividing the first gingival band into at least one first region comprising a first plurality of cells and associating at least one first color value therewith;
    analyzing the at least one first color value;
    identifying a second gingival margin of at least one second gingival tissue image;
    creating a second gingival band, the second gingival band including the second gingival margin and a second ending boundary;
    dividing the second gingival band into at least one second region comprising a second plurality of cells and associating at least one second color value therewith;
    analyzing the at least one second color value;
    comparing the at least one color value to the at least one second color value to obtain a mathematical value;
    associating a display color with the mathematical value; and
    displaying the display color on a display image.

2. The method of claim 1, wherein the oral cavity soft tissue comprises at least one of a marginal gingiva, a gingival sulcus, an inter-dental gingiva, gingival gum structure on lingual or buccal surfaces up to and including muco-gingival junction, a palate, and gingival tissues.

3. The method of claim 1, wherein the oral cavity soft tissue includes at least one of a maxillary arch tissue, a mandibular arch tissue, or soft tissue adjacent to at least one of a central incisor, a lateral incisor, or a canine.

4. The method of claim 1, wherein the at least one first region includes at least one first pixel, the at least one first pixel including the at least one first color value.

5. The method of claim 1, wherein the first gingival margin includes a line indicating a junction between a tooth and the gingival tissue.

6. The method of claim 1, wherein the at least one first color value includes one of an R value, a G value, and a B value.

7. The method of claim 1, wherein analyzing the at least one first color value comprises deriving statistics from at least one of an R value, a G value, and a B value.

8. The method of claim 1, wherein analyzing the at least one first color value comprises averaging one of an R value, a G value, and a B value for the at least one first region.

9. The method of claim 1, wherein the display color is displayed at a portion of the display image that corresponds with the first region of the at least one first gingival tissue image.

10. The method of claim 1, wherein the first and second gingival tissue images are from the same subject and wherein the second gingival tissue image is captured after the first gingival tissue image.

11. The method of claim 1, wherein the second gingival tissue image is captured between about 1 day and about 6 months after the first gingival tissue image.

12. The method of claim 1, wherein the display image is an image of at least a portion of one of a maxillary arch or a mandibular arch.

13. The method of claim 1, wherein the oral cavity soft tissue comprises at least one of maxillary arch gingival tissue or mandibular arch gingival tissue.

14. The method of claim 1, further comprising recording a plurality of gingival tissue images.

15. The method of claim 1, further comprising recording a plurality of gingival tissue images, the plurality of gingival tissue images originating from a single subject.

16. The method of claim 1, further comprising creating comparison data from a plurality of gingival tissue images.

17. The method of claim 1, further comprising creating comparison data from a plurality of gingival tissue images, the plurality of gingival tissue images comprising images before a treatment and images after the treatment.

18. The method of claim 1, further comprising creating comparison data from a plurality of gingival tissue images, the plurality of gingival tissue images comprising images before a product use and images after the product use.

19. The method of claim 1, further comprising creating comparison data from a plurality of gingival tissue images, the plurality of gingival tissue images comprising images before a regimen and images after the regimen.

20. The method of claim 1, wherein analyzing the at least one color value comprises statistically comparing the at least one region of the first gingival tissue image with the at least one region of a plurality of second gingival tissue images;
    wherein the plurality of second gingival tissue images is later in time than the first gingival tissue image.

21. The method of claim 1, wherein analyzing the at least one color value comprises statistically analyzing a plurality of gingival tissue images over time using one of a paired t-test, or descriptive statistics.

22. The method of claim 1, further comprising calculating a plurality differences for a plurality of first color values and a plurality of second color values, wherein the plurality of differences are statistically manipulated to calculate a representative statistical value having a representative display color associated therewith.

23. The method of claim 22, wherein the plurality of first color values and the plurality of second color values are from a plurality of subjects.

24. The method of claim 1, further comprising recording a plurality of gingival tissue images, the plurality of gingival tissue images originating from a plurality of subjects.

25. The method of claim 24, wherein the plurality of subjects are part of a single study involving one or more oral care products.

26. The method of claim 1, further comprising:
    capturing the oral care soft tissue image at a first location;
    sending the oral care soft tissue image to a second location;

wherein analyzing the at least one color value comprises analyzing the at least one first color value at the second location.

27. The method of claim 26, wherein sending the oral care soft tissue image to a second location comprises sending the oral care soft tissue image by one of internet, a local network, a facsimile, an e-mail, a satellite link, or a postal service.

28. The method of claim 1, used to measure the efficacy of at least one of a product, regimen, technique, or demographic on gingival health.

29. The method of claim 28, wherein measuring the efficacy of at least one of a product, regimen, technique, or demographic on gingival health comprises comparing a plurality of gingival tissue images from a first subject with a plurality of gingival tissue images from at least one second subject.

30. The method of claim 28, wherein measuring the efficacy of at least one of a product, regimen, technique, or demographic on gingival health includes comparing a plurality of gingival tissue images from a subject, the plurality of gingival tissue images from the subject taken over a period of time.

31. The method of claim 1, wherein the at least one first region includes at least one gingival sub-band.

32. The method of claim 31, further comprising sub-dividing the at least one gingival sub-band into a plurality of cells.

33. The method of claim 31, wherein the gingival sub-band includes a sub-band boundary.

34. The method of claim 33, wherein the sub-band boundary is positioned generally parallel to the gingival margin.

* * * * *